US011285963B2

(12) United States Patent
Raichelgauz

(10) Patent No.: US 11,285,963 B2
(45) Date of Patent: Mar. 29, 2022

(54) DRIVER-BASED PREDICTION OF DANGEROUS EVENTS

(71) Applicant: CARTICA AI LTD., Tel Aviv (IL)

(72) Inventor: Igal Raichelgauz, Tel Aviv (IL)

(73) Assignee: CARTICA AI LTD., Tel Aviv (IL)

( * ) Notice: Subject to any disclaimer, the term of this patent is extended or adjusted under 35 U.S.C. 154(b) by 43 days.

(21) Appl. No.: 16/780,931

(22) Filed: Feb. 4, 2020

(65) Prior Publication Data

US 2020/0283003 A1 Sep. 10, 2020

Related U.S. Application Data

(60) Provisional application No. 62/816,146, filed on Mar. 10, 2019.

(51) Int. Cl.
| | |
|---|---|
| *B60W 40/09* | (2012.01) |
| *B60W 50/00* | (2006.01) |
| *A61B 5/00* | (2006.01) |
| *B60W 40/08* | (2012.01) |

(52) U.S. Cl.
CPC ........... *B60W 40/09* (2013.01); *A61B 5/0006* (2013.01); *B60W 50/0097* (2013.01); *B60W 2040/0827* (2013.01); *B60W 2040/0872* (2013.01); *B60W 2540/221* (2020.02); *B60W 2540/225* (2020.02); *B60W 2540/26* (2013.01)

(58) Field of Classification Search
CPC .. B60W 40/08; B60W 40/09; B60W 50/0097; B60W 50/14; B60W 2540/221; B60W 2540/225; B60W 2540/26; B60W 2040/0827; B60W 2040/0872; A61B 5/0006; G05D 1/0088; G05D 2201/0213; G06K 9/00845; G06N 20/00

See application file for complete search history.

(56) References Cited

U.S. PATENT DOCUMENTS

| | | | |
|---|---|---|---|
| 4,733,353 | A | 3/1988 | Jaswa |
| 4,932,645 | A | 6/1990 | Schorey et al. |
| 4,972,363 | A | 11/1990 | Nguyen et al. |
| 5,078,501 | A | 1/1992 | Hekker et al. |
| 5,214,746 | A | 5/1993 | Fogel et al. |

(Continued)

FOREIGN PATENT DOCUMENTS

| | | |
|---|---|---|
| EP | 1085464 A3 | 1/2007 |
| WO | 0231764 A2 | 4/2002 |

(Continued)

OTHER PUBLICATIONS

Jasinschi et al., "A Probabilistic Layered Framework for Integrating Multimedia Content and Context Information", 2002, IEEE, p. 2057-2060. (Year: 2002).

(Continued)

*Primary Examiner* — Orlando Bousono
(74) *Attorney, Agent, or Firm* — Reches Patents

(57) ABSTRACT

A method that includes (a) monitoring a physiological state of a driver to provide physiological state information; (b) receiving or generating an indication about a dangerous event; (c) searching for a predicting physiological parameter that is associated with a predicting pattern that was indicative of an occurrence of the dangerous event; and (d) responding to the when finding of the predicting physiological parameter.

19 Claims, 8 Drawing Sheets

(56) References Cited

U.S. PATENT DOCUMENTS

| | | |
|---|---|---|
| 5,307,451 A | 4/1994 | Clark |
| 5,412,564 A | 5/1995 | Ecer |
| 5,436,653 A | 7/1995 | Ellis et al. |
| 5,568,181 A | 10/1996 | Greenwood et al. |
| 5,638,425 A | 6/1997 | Meador, I et al. |
| 5,745,678 A | 4/1998 | Herzberg et al. |
| 5,754,938 A | 5/1998 | Herz et al. |
| 5,763,069 A | 6/1998 | Jordan |
| 5,806,061 A | 9/1998 | Chaudhuri et al. |
| 5,835,087 A | 11/1998 | Herz et al. |
| 5,835,901 A | 11/1998 | Duvoisin et al. |
| 5,852,435 A | 12/1998 | Vigneaux et al. |
| 5,870,754 A | 2/1999 | Dimitrova et al. |
| 5,873,080 A | 2/1999 | Coden et al. |
| 5,887,193 A | 3/1999 | Takahashi et al. |
| 5,926,812 A | 7/1999 | Hilsenrath et al. |
| 5,978,754 A | 11/1999 | Kumano |
| 5,991,306 A | 11/1999 | Burns et al. |
| 6,052,481 A | 4/2000 | Grajski et al. |
| 6,070,167 A | 5/2000 | Qian et al. |
| 6,076,088 A | 6/2000 | Paik et al. |
| 6,122,628 A | 9/2000 | Castelli et al. |
| 6,128,651 A | 10/2000 | Cezar |
| 6,137,911 A | 10/2000 | Zhilyaev |
| 6,144,767 A | 11/2000 | Bottou et al. |
| 6,147,636 A | 11/2000 | Gershenson |
| 6,163,510 A | 12/2000 | Lee et al. |
| 6,243,375 B1 | 6/2001 | Speicher |
| 6,243,713 B1 | 6/2001 | Nelson et al. |
| 6,275,599 B1 | 8/2001 | Adler et al. |
| 6,314,419 B1 | 11/2001 | Faisal |
| 6,329,986 B1 | 12/2001 | Cheng |
| 6,381,656 B1 | 4/2002 | Shankman |
| 6,411,229 B2 | 6/2002 | Kobayashi |
| 6,422,617 B1 | 7/2002 | Fukumoto et al. |
| 6,507,672 B1 | 1/2003 | Watkins et al. |
| 6,523,046 B2 | 2/2003 | Liu et al. |
| 6,524,861 B1 | 2/2003 | Anderson |
| 6,546,405 B2 | 4/2003 | Gupta et al. |
| 6,550,018 B1 | 4/2003 | Abonamah et al. |
| 6,557,042 B1 | 4/2003 | He et al. |
| 6,594,699 B1 | 7/2003 | Sahai et al. |
| 6,601,026 B2 | 7/2003 | Appelt et al. |
| 6,611,628 B1 | 8/2003 | Sekiguchi et al. |
| 6,618,711 B1 | 9/2003 | Ananth |
| 6,640,015 B1 | 10/2003 | Lafruit |
| 6,643,620 B1 | 11/2003 | Contolini et al. |
| 6,643,643 B1 | 11/2003 | Lee et al. |
| 6,665,657 B1 | 12/2003 | Dibachi |
| 6,681,032 B2 | 1/2004 | Bortolussi et al. |
| 6,704,725 B1 | 3/2004 | Lee |
| 6,732,149 B1 | 5/2004 | Kephart |
| 6,742,094 B2 | 5/2004 | Igari |
| 6,751,363 B1 | 6/2004 | Natsev et al. |
| 6,751,613 B1 | 6/2004 | Lee et al. |
| 6,754,435 B2 | 6/2004 | Kim |
| 6,763,069 B1 | 7/2004 | Divakaran et al. |
| 6,763,519 B1 | 7/2004 | McColl et al. |
| 6,774,917 B1 | 8/2004 | Foote et al. |
| 6,795,818 B1 | 9/2004 | Lee |
| 6,804,356 B1 | 10/2004 | Krishnamachari |
| 6,813,395 B1 | 11/2004 | Kinjo |
| 6,819,797 B1 | 11/2004 | Smith et al. |
| 6,877,134 B1 | 4/2005 | Fuller et al. |
| 6,901,207 B1 | 5/2005 | Watkins |
| 6,938,025 B1 | 8/2005 | Lulich et al. |
| 6,985,172 B1 | 1/2006 | Rigney et al. |
| 7,013,051 B2 | 3/2006 | Sekiguchi et al. |
| 7,020,654 B1 | 3/2006 | Najmi |
| 7,023,979 B1 | 4/2006 | Wu et al. |
| 7,043,473 B1 | 5/2006 | Rassool et al. |
| 7,158,681 B2 | 1/2007 | Persiantsev |
| 7,215,828 B2 | 5/2007 | Luo |
| 7,260,564 B1 | 8/2007 | Lynn et al. |
| 7,289,643 B2 | 10/2007 | Brunk et al. |
| 7,299,261 B1 | 11/2007 | Oliver et al. |
| 7,302,089 B1 | 11/2007 | Smits |
| 7,302,117 B2 | 11/2007 | Sekiguchi et al. |
| 7,313,805 B1 | 12/2007 | Rosin et al. |
| 7,340,358 B2 | 3/2008 | Yoneyama |
| 7,346,629 B2 | 3/2008 | Kapur et al. |
| 7,353,224 B2 | 4/2008 | Chen et al. |
| 7,376,672 B2 | 5/2008 | Weare |
| 7,383,179 B2 | 6/2008 | Alves et al. |
| 7,433,895 B2 | 10/2008 | Li et al. |
| 7,464,086 B2 | 12/2008 | Black et al. |
| 7,529,659 B2 | 5/2009 | Wold |
| 7,657,100 B2 | 2/2010 | Gokturk et al. |
| 7,660,468 B2 | 2/2010 | Gokturk et al. |
| 7,801,893 B2 | 9/2010 | Gulli |
| 7,805,446 B2 | 9/2010 | Potok et al. |
| 7,860,895 B1 | 12/2010 | Scofield et al. |
| 7,872,669 B2 | 1/2011 | Darrell et al. |
| 7,921,288 B1 | 4/2011 | Hildebrand |
| 7,933,407 B2 | 4/2011 | Keidar et al. |
| 8,023,739 B2 | 9/2011 | Hohimer et al. |
| 8,266,185 B2 | 9/2012 | Raichelgauz et al. |
| 8,275,764 B2 | 9/2012 | Jeon |
| 8,285,718 B1 | 10/2012 | Ong et al. |
| 8,312,031 B2 | 11/2012 | Raichelgauz et al. |
| 8,315,442 B2 | 11/2012 | Gokturk et al. |
| 8,345,982 B2 | 1/2013 | Gokturk et al. |
| 8,386,400 B2 | 2/2013 | Raichelgauz et al. |
| 8,396,876 B2 | 3/2013 | Kennedy et al. |
| 8,418,206 B2 | 4/2013 | Bryant et al. |
| RE44,225 E | 5/2013 | Aviv |
| 8,442,321 B1 | 5/2013 | Chang et al. |
| 8,457,827 B1 | 6/2013 | Ferguson et al. |
| 8,495,489 B1 | 7/2013 | Everingham |
| 8,527,978 B1 | 9/2013 | Sallam |
| 8,634,980 B1 | 1/2014 | Urmson |
| 8,635,531 B2 | 1/2014 | Graham et al. |
| 8,655,801 B2 | 2/2014 | Raichelgauz et al. |
| 8,655,878 B1 | 2/2014 | Kulkarni et al. |
| 8,781,152 B2 | 7/2014 | Momeyer |
| 8,782,077 B1 | 7/2014 | Rowley |
| 8,799,195 B2 | 8/2014 | Raichelgauz et al. |
| 8,799,196 B2 | 8/2014 | Raichelquaz et al. |
| 8,818,916 B2 | 8/2014 | Raichelgauz et al. |
| 8,868,861 B2 | 10/2014 | Shimizu et al. |
| 8,886,648 B1 | 11/2014 | Procopio et al. |
| 8,954,887 B1 | 2/2015 | Tseng et al. |
| 8,990,199 B1 | 3/2015 | Ramesh et al. |
| 9,009,086 B2 | 4/2015 | Raichelgauz et al. |
| 9,104,747 B2 | 8/2015 | Raichelgauz et al. |
| 9,165,406 B1 | 10/2015 | Gray et al. |
| 9,298,763 B1 | 3/2016 | Zack |
| 9,311,308 B2 | 4/2016 | Sankarasubramaniam et al. |
| 9,323,754 B2 | 4/2016 | Ramanathan et al. |
| 9,440,647 B1 | 9/2016 | Sucan |
| 9,466,068 B2 | 10/2016 | Raichelgauz et al. |
| 9,646,006 B2 | 5/2017 | Raichelgauz et al. |
| 9,679,062 B2 | 6/2017 | Schillings et al. |
| 9,734,533 B1 | 8/2017 | Givot |
| 9,807,442 B2 | 10/2017 | Bhatia et al. |
| 9,875,445 B2 | 1/2018 | Amer et al. |
| 9,984,369 B2 | 5/2018 | Li et al. |
| 10,133,947 B2 | 11/2018 | Yang |
| 10,347,122 B2 | 7/2019 | Takenaka |
| 10,491,885 B1 | 11/2019 | Hicks |
| 10,762,785 B1 * | 9/2020 | Dewey ............... B62D 15/0265 |
| 2001/0019633 A1 | 9/2001 | Tenze et al. |
| 2001/0034219 A1 | 10/2001 | Hewitt et al. |
| 2001/0038876 A1 | 11/2001 | Anderson |
| 2002/0004743 A1 | 1/2002 | Kutaragi et al. |
| 2002/0010682 A1 | 1/2002 | Johnson |
| 2002/0010715 A1 | 1/2002 | Chinn et al. |
| 2002/0019881 A1 | 2/2002 | Bokhari et al. |
| 2002/0032677 A1 | 3/2002 | Morgenthaler et al. |
| 2002/0038299 A1 | 3/2002 | Zernik et al. |
| 2002/0042914 A1 | 4/2002 | Walker et al. |
| 2002/0072935 A1 | 6/2002 | Rowse et al. |
| 2002/0087530 A1 | 7/2002 | Smith et al. |
| 2002/0087828 A1 | 7/2002 | Arimilli et al. |

(56) References Cited

U.S. PATENT DOCUMENTS

| | | |
|---|---|---|
| 2002/0091947 A1 | 7/2002 | Nakamura |
| 2002/0107827 A1 | 8/2002 | Benitez-Jimenez et al. |
| 2002/0113812 A1 | 8/2002 | Walker et al. |
| 2002/0126002 A1 | 9/2002 | Patchell |
| 2002/0126872 A1 | 9/2002 | Brunk et al. |
| 2002/0129140 A1 | 9/2002 | Peled et al. |
| 2002/0147637 A1 | 10/2002 | Kraft et al. |
| 2002/0157116 A1 | 10/2002 | Jasinschi |
| 2002/0163532 A1 | 11/2002 | Thomas et al. |
| 2002/0174095 A1 | 11/2002 | Lulich et al. |
| 2002/0184505 A1 | 12/2002 | Mihcak et al. |
| 2003/0004966 A1 | 1/2003 | Bolle et al. |
| 2003/0005432 A1 | 1/2003 | Ellis et al. |
| 2003/0037010 A1 | 2/2003 | Schmelzer |
| 2003/0041047 A1 | 2/2003 | Chang et al. |
| 2003/0043045 A1* | 3/2003 | Yasushi .............. A61B 5/7275 340/576 |
| 2003/0089216 A1 | 5/2003 | Birmingham et al. |
| 2003/0093790 A1 | 5/2003 | Logan et al. |
| 2003/0101150 A1 | 5/2003 | Agnihotri et al. |
| 2003/0105739 A1 | 6/2003 | Essafi et al. |
| 2003/0110236 A1 | 6/2003 | Yang et al. |
| 2003/0115191 A1 | 6/2003 | Copperman et al. |
| 2003/0126147 A1 | 7/2003 | Essafi et al. |
| 2003/0140257 A1 | 7/2003 | Peterka et al. |
| 2003/0165269 A1 | 9/2003 | Fedorovskaya et al. |
| 2003/0174859 A1 | 9/2003 | Kim |
| 2003/0184598 A1 | 10/2003 | Graham |
| 2003/0200217 A1 | 10/2003 | Ackerman |
| 2003/0217335 A1 | 11/2003 | Chung et al. |
| 2003/0229531 A1 | 12/2003 | Heckerman et al. |
| 2004/0059736 A1 | 3/2004 | Willse |
| 2004/0091111 A1 | 5/2004 | Levy |
| 2004/0095376 A1 | 5/2004 | Graham et al. |
| 2004/0098671 A1 | 5/2004 | Graham et al. |
| 2004/0111432 A1 | 6/2004 | Adams et al. |
| 2004/0117638 A1 | 6/2004 | Monroe |
| 2004/0128511 A1 | 7/2004 | Sun et al. |
| 2004/0153426 A1 | 8/2004 | Nugent |
| 2004/0162820 A1 | 8/2004 | James et al. |
| 2004/0230572 A1 | 11/2004 | Omoigui |
| 2004/0267774 A1 | 12/2004 | Lin et al. |
| 2005/0021394 A1 | 1/2005 | Miedema et al. |
| 2005/0080788 A1 | 4/2005 | Murata |
| 2005/0114198 A1 | 5/2005 | Koningstein et al. |
| 2005/0131884 A1 | 6/2005 | Gross et al. |
| 2005/0163375 A1 | 7/2005 | Grady |
| 2005/0172130 A1 | 8/2005 | Roberts |
| 2005/0177372 A1 | 8/2005 | Wang et al. |
| 2005/0193015 A1 | 9/2005 | Logston |
| 2005/0226511 A1 | 10/2005 | Short |
| 2005/0238198 A1 | 10/2005 | Brown et al. |
| 2005/0238238 A1 | 10/2005 | Xu et al. |
| 2005/0249398 A1 | 11/2005 | Khamene et al. |
| 2005/0256820 A1 | 11/2005 | Dugan et al. |
| 2005/0262428 A1 | 11/2005 | Little et al. |
| 2005/0281439 A1 | 12/2005 | Lange |
| 2005/0289163 A1 | 12/2005 | Gordon et al. |
| 2005/0289590 A1 | 12/2005 | Cheok et al. |
| 2006/0004745 A1 | 1/2006 | Kuhn et al. |
| 2006/0015580 A1 | 1/2006 | Gabriel et al. |
| 2006/0020958 A1 | 1/2006 | Allamanche et al. |
| 2006/0033163 A1 | 2/2006 | Chen |
| 2006/0050993 A1 | 3/2006 | Stentiford |
| 2006/0069668 A1 | 3/2006 | Braddy et al. |
| 2006/0080311 A1 | 4/2006 | Potok et al. |
| 2006/0100987 A1 | 5/2006 | Leurs |
| 2006/0112035 A1 | 5/2006 | Cecchi et al. |
| 2006/0120626 A1 | 6/2006 | Perlmutter |
| 2006/0129822 A1 | 6/2006 | Snijder et al. |
| 2006/0217818 A1 | 9/2006 | Fujiwara |
| 2006/0217828 A1 | 9/2006 | Hicken |
| 2006/0218191 A1 | 9/2006 | Gopalakrishnan |
| 2006/0224529 A1 | 10/2006 | Kermani |
| 2006/0236343 A1 | 10/2006 | Chang |
| 2006/0242130 A1 | 10/2006 | Sadri et al. |
| 2006/0248558 A1 | 11/2006 | Barton et al. |
| 2006/0251338 A1 | 11/2006 | Gokturk et al. |
| 2006/0251339 A1 | 11/2006 | Gokturk |
| 2006/0253423 A1 | 11/2006 | McLane et al. |
| 2006/0288002 A1 | 12/2006 | Epstein et al. |
| 2007/0022374 A1 | 1/2007 | Huang et al. |
| 2007/0033170 A1 | 2/2007 | Sull et al. |
| 2007/0038614 A1 | 2/2007 | Guha |
| 2007/0042757 A1 | 2/2007 | Jung et al. |
| 2007/0061302 A1 | 3/2007 | Ramer et al. |
| 2007/0067304 A1 | 3/2007 | Ives |
| 2007/0074147 A1 | 3/2007 | Wold |
| 2007/0083611 A1 | 4/2007 | Farago et al. |
| 2007/0091106 A1 | 4/2007 | Moroney |
| 2007/0130159 A1 | 6/2007 | Gulli et al. |
| 2007/0136782 A1 | 6/2007 | Ramaswamy et al. |
| 2007/0156720 A1 | 7/2007 | Maren |
| 2007/0196013 A1 | 8/2007 | Li |
| 2007/0244902 A1 | 10/2007 | Seide et al. |
| 2007/0253594 A1 | 11/2007 | Lu et al. |
| 2007/0298152 A1 | 12/2007 | Baets |
| 2008/0049789 A1 | 2/2008 | Vedantham et al. |
| 2008/0072256 A1 | 3/2008 | Boicey et al. |
| 2008/0079729 A1 | 4/2008 | Brailovsky |
| 2008/0109433 A1 | 5/2008 | Rose |
| 2008/0152231 A1 | 6/2008 | Gokturk |
| 2008/0159622 A1 | 7/2008 | Agnihotri et al. |
| 2008/0165861 A1 | 7/2008 | Wen et al. |
| 2008/0166020 A1 | 7/2008 | Kosaka |
| 2008/0201299 A1 | 8/2008 | Lehikoinen et al. |
| 2008/0201314 A1 | 8/2008 | Smith et al. |
| 2008/0201361 A1 | 8/2008 | Castro et al. |
| 2008/0228995 A1 | 9/2008 | Tan et al. |
| 2008/0237359 A1 | 10/2008 | Silverbrook et al. |
| 2008/0247543 A1 | 10/2008 | Mick et al. |
| 2008/0253737 A1 | 10/2008 | Kimura et al. |
| 2008/0263579 A1 | 10/2008 | Mears et al. |
| 2008/0270373 A1 | 10/2008 | Oostveen et al. |
| 2008/0270569 A1 | 10/2008 | McBride |
| 2008/0294278 A1 | 11/2008 | Borgeson |
| 2008/0307454 A1 | 12/2008 | Ahanger et al. |
| 2008/0313140 A1 | 12/2008 | Pereira et al. |
| 2009/0022472 A1 | 1/2009 | Bronstein |
| 2009/0024641 A1 | 1/2009 | Quigley et al. |
| 2009/0034791 A1 | 2/2009 | Doretto |
| 2009/0037088 A1 | 2/2009 | Taguchi |
| 2009/0040054 A1* | 2/2009 | Wang .................. B60W 30/095 340/576 |
| 2009/0043637 A1 | 2/2009 | Eder |
| 2009/0043818 A1 | 2/2009 | Raichelgauz |
| 2009/0080759 A1 | 3/2009 | Bhaskar |
| 2009/0096634 A1 | 4/2009 | Emam et al. |
| 2009/0125544 A1 | 5/2009 | Brindley |
| 2009/0157575 A1 | 6/2009 | Schobben et al. |
| 2009/0165031 A1 | 6/2009 | Li et al. |
| 2009/0172030 A1 | 7/2009 | Schiff et al. |
| 2009/0208106 A1 | 8/2009 | Dunlop et al. |
| 2009/0208118 A1 | 8/2009 | Csurka |
| 2009/0216761 A1 | 8/2009 | Raichelgauz |
| 2009/0220138 A1 | 9/2009 | Zhang et al. |
| 2009/0245573 A1 | 10/2009 | Saptharishi et al. |
| 2009/0254572 A1 | 10/2009 | Redlich et al. |
| 2009/0278934 A1 | 11/2009 | Ecker |
| 2009/0282218 A1 | 11/2009 | Raichelgauz et al. |
| 2009/0297048 A1 | 12/2009 | Slotine et al. |
| 2010/0042646 A1 | 2/2010 | Raichelqauz |
| 2010/0082684 A1 | 4/2010 | Churchill |
| 2010/0104184 A1 | 4/2010 | Bronstein et al. |
| 2010/0111408 A1 | 5/2010 | Matsuhira |
| 2010/0125569 A1 | 5/2010 | Nair et al. |
| 2010/0162405 A1 | 6/2010 | Cook et al. |
| 2010/0191391 A1 | 7/2010 | Zeng |
| 2010/0198626 A1 | 8/2010 | Cho et al. |
| 2010/0212015 A1 | 8/2010 | Jin et al. |
| 2010/0284604 A1 | 11/2010 | Chrysanthakopoulos |
| 2010/0293057 A1 | 11/2010 | Haveliwala et al. |
| 2010/0306193 A1 | 12/2010 | Pereira |
| 2010/0312736 A1 | 12/2010 | Kello |

(56) References Cited

U.S. PATENT DOCUMENTS

| | | |
|---|---|---|
| 2010/0318493 A1 | 12/2010 | Wessling |
| 2010/0325138 A1 | 12/2010 | Lee et al. |
| 2010/0325581 A1 | 12/2010 | Finkelstein et al. |
| 2011/0029620 A1 | 2/2011 | Bonforte |
| 2011/0035373 A1 | 2/2011 | Berg et al. |
| 2011/0038545 A1 | 2/2011 | Bober |
| 2011/0055585 A1 | 3/2011 | Lee |
| 2011/0164180 A1 | 7/2011 | Lee |
| 2011/0164810 A1 | 7/2011 | Zang et al. |
| 2011/0216209 A1 | 9/2011 | Fredlund et al. |
| 2011/0218946 A1 | 9/2011 | Stern et al. |
| 2011/0246566 A1 | 10/2011 | Kashef |
| 2011/0276680 A1 | 11/2011 | Rimon |
| 2011/0296315 A1 | 12/2011 | Lin et al. |
| 2012/0131454 A1 | 5/2012 | Shah |
| 2012/0133497 A1 | 5/2012 | Sasaki |
| 2012/0136853 A1 | 5/2012 | Kennedy et al. |
| 2012/0167133 A1 | 6/2012 | Carroll et al. |
| 2012/0179642 A1 | 7/2012 | Sweeney et al. |
| 2012/0179751 A1 | 7/2012 | Ahn |
| 2012/0185445 A1 | 7/2012 | Borden et al. |
| 2012/0207346 A1 | 8/2012 | Kohli et al. |
| 2012/0221470 A1 | 8/2012 | Lyon |
| 2012/0227074 A1 | 9/2012 | Hill et al. |
| 2012/0239690 A1 | 9/2012 | Asikainen et al. |
| 2012/0239694 A1 | 9/2012 | Avner et al. |
| 2012/0265735 A1 | 10/2012 | McMillan et al. |
| 2012/0294514 A1 | 11/2012 | Saunders et al. |
| 2012/0299961 A1 | 11/2012 | Ramkumar et al. |
| 2012/0301105 A1 | 11/2012 | Rehg et al. |
| 2012/0331011 A1 | 12/2012 | Raichelgauz et al. |
| 2013/0043990 A1 | 2/2013 | Al-Jafar |
| 2013/0066856 A1 | 3/2013 | Ong et al. |
| 2013/0067364 A1 | 3/2013 | Berntson et al. |
| 2013/0086499 A1 | 4/2013 | Dyor et al. |
| 2013/0089248 A1 | 4/2013 | Remiszewski et al. |
| 2013/0103814 A1 | 4/2013 | Carrasco |
| 2013/0151522 A1 | 6/2013 | Aggarwal et al. |
| 2013/0159298 A1 | 6/2013 | Mason et al. |
| 2013/0212493 A1 | 8/2013 | Krishnamurthy |
| 2013/0226820 A1 | 8/2013 | Sedota, Jr. |
| 2013/0226930 A1 | 8/2013 | Arngren et al. |
| 2013/0227023 A1 | 8/2013 | Raichelgauz et al. |
| 2013/0283401 A1 | 10/2013 | Pabla et al. |
| 2013/0346412 A1 | 12/2013 | Raichelgauz et al. |
| 2014/0019264 A1 | 1/2014 | Wachman et al. |
| 2014/0025692 A1 | 1/2014 | Pappas |
| 2014/0059443 A1 | 2/2014 | Tabe |
| 2014/0095425 A1 | 4/2014 | Sipple |
| 2014/0111647 A1 | 4/2014 | Atsmon |
| 2014/0125703 A1 | 5/2014 | Roveta et al. |
| 2014/0147829 A1 | 5/2014 | Jerauld |
| 2014/0149918 A1 | 5/2014 | Asokan et al. |
| 2014/0152698 A1 | 6/2014 | Kim et al. |
| 2014/0156691 A1 | 6/2014 | Conwell |
| 2014/0169681 A1 | 6/2014 | Drake |
| 2014/0176604 A1 | 6/2014 | Venkitaraman et al. |
| 2014/0193077 A1 | 7/2014 | Shiiyama et al. |
| 2014/0198986 A1 | 7/2014 | Marchesotti |
| 2014/0201330 A1 | 7/2014 | Lozano Lopez |
| 2014/0250032 A1 | 9/2014 | Huang et al. |
| 2014/0282655 A1 | 9/2014 | Roberts |
| 2014/0300722 A1 | 10/2014 | Garcia |
| 2014/0330830 A1 | 11/2014 | Raichelgauz et al. |
| 2014/0341476 A1 | 11/2014 | Kulick et al. |
| 2014/0363044 A1 | 12/2014 | Williams et al. |
| 2014/0379477 A1 | 12/2014 | Sheinfeld |
| 2015/0033150 A1 | 1/2015 | Lee |
| 2015/0052089 A1 | 2/2015 | Kozloski et al. |
| 2015/0100562 A1 | 4/2015 | Kohlmeier et al. |
| 2015/0117784 A1 | 4/2015 | Lin |
| 2015/0120627 A1 | 4/2015 | Hunzinger et al. |
| 2015/0127516 A1 | 5/2015 | Studnitzer et al. |
| 2015/0134688 A1 | 5/2015 | Jing |
| 2015/0248586 A1 | 9/2015 | Gaidon et al. |
| 2015/0254344 A1 | 9/2015 | Kulkarni et al. |
| 2015/0286742 A1 | 10/2015 | Zhang et al. |
| 2015/0286872 A1 | 10/2015 | Medioni et al. |
| 2015/0324356 A1 | 11/2015 | Gutierrez et al. |
| 2015/0332588 A1 | 11/2015 | Bulan et al. |
| 2015/0363644 A1 | 12/2015 | Wnuk |
| 2016/0007083 A1 | 1/2016 | Gurha |
| 2016/0026707 A1 | 1/2016 | Ong et al. |
| 2016/0132194 A1 | 5/2016 | Grue et al. |
| 2016/0210525 A1 | 7/2016 | Yang |
| 2016/0221592 A1 | 8/2016 | Puttagunta |
| 2016/0275766 A1 | 9/2016 | Venetianer et al. |
| 2016/0306798 A1 | 10/2016 | Guo et al. |
| 2016/0342683 A1 | 11/2016 | Kwon |
| 2016/0357188 A1 | 12/2016 | Ansari |
| 2017/0017638 A1 | 1/2017 | Satyavarta et al. |
| 2017/0032257 A1 | 2/2017 | Sharifi |
| 2017/0041254 A1 | 2/2017 | Agara Venkatesha Rao |
| 2017/0109602 A1 | 4/2017 | Kim |
| 2017/0154241 A1 | 6/2017 | Shambik et al. |
| 2017/0176198 A1* | 6/2017 | Tatourian ............ G06K 9/00845 |
| 2017/0255620 A1 | 9/2017 | Raichelgauz |
| 2017/0262437 A1 | 9/2017 | Raichelgauz |
| 2017/0323568 A1 | 11/2017 | Inoue |
| 2018/0081368 A1 | 3/2018 | Watanabe |
| 2018/0101177 A1 | 4/2018 | Cohen |
| 2018/0108258 A1 | 4/2018 | Dilger |
| 2018/0157903 A1 | 6/2018 | Tu et al. |
| 2018/0157916 A1 | 6/2018 | Doumbouya |
| 2018/0158323 A1 | 6/2018 | Takenaka |
| 2018/0189613 A1 | 7/2018 | Wolf et al. |
| 2018/0204111 A1 | 7/2018 | Zadeh |
| 2018/0373929 A1 | 12/2018 | Ye |
| 2019/0005726 A1 | 1/2019 | Nakano |
| 2019/0039627 A1 | 2/2019 | Yamamoto |
| 2019/0043274 A1 | 2/2019 | Hayakawa |
| 2019/0045244 A1 | 2/2019 | Balakrishnan |
| 2019/0056718 A1 | 2/2019 | Satou |
| 2019/0065951 A1 | 2/2019 | Luo |
| 2019/0096135 A1 | 3/2019 | Mutto et al. |
| 2019/0102689 A1* | 4/2019 | Lassoued ............ G07C 5/0841 |
| 2019/0171912 A1 | 6/2019 | Vallespi-Gonzalez et al. |
| 2019/0188501 A1 | 6/2019 | Ryu |
| 2019/0220011 A1 | 7/2019 | Della Penna |
| 2019/0279046 A1 | 9/2019 | Han et al. |
| 2019/0304102 A1 | 10/2019 | Chen et al. |
| 2019/0317513 A1 | 10/2019 | Zhang |
| 2019/0364492 A1 | 11/2019 | Azizi |
| 2019/0382025 A1* | 12/2019 | Mena Benito ....... A61B 5/6802 |
| 2019/0384303 A1 | 12/2019 | Muller |
| 2019/0384312 A1 | 12/2019 | Herbach |
| 2019/0385460 A1 | 12/2019 | Magzimof |
| 2019/0389459 A1 | 12/2019 | Berntorp |
| 2020/0004248 A1 | 1/2020 | Healey |
| 2020/0004251 A1 | 1/2020 | Zhu |
| 2020/0004265 A1 | 1/2020 | Zhu |
| 2020/0005631 A1 | 1/2020 | Visintainer |
| 2020/0018606 A1 | 1/2020 | Wolcott |
| 2020/0018618 A1 | 1/2020 | Ozog |
| 2020/0020212 A1 | 1/2020 | Song |
| 2020/0050973 A1 | 2/2020 | Stenneth |
| 2020/0070840 A1* | 3/2020 | Gunaratne ............ B60K 28/06 |
| 2020/0073977 A1 | 3/2020 | Montemerlo |
| 2020/0090484 A1 | 3/2020 | Chen |
| 2020/0097756 A1 | 3/2020 | Hashimoto |
| 2020/0133307 A1 | 4/2020 | Kelkar |
| 2020/0043326 A1 | 6/2020 | Tao |

FOREIGN PATENT DOCUMENTS

| | | |
|---|---|---|
| WO | 2003067467 A1 | 8/2003 |
| WO | 2005027457 A1 | 3/2005 |
| WO | 2007049282 A2 | 5/2007 |
| WO | 2014076002 A1 | 5/2014 |
| WO | 2014137337 A1 | 9/2014 |
| WO | 2016040376 A1 | 3/2016 |
| WO | 2016070193 A1 | 5/2016 |

(56) References Cited

FOREIGN PATENT DOCUMENTS

OTHER PUBLICATIONS

Jones et al., "Contextual Dynamics of Group-Based Sharing Decisions", 2011, University of Bath, p. 1777-1786. (Year: 2011).
Iwamoto, "Image Signature Robust to Caption Superimpostion for Video Sequence Identification", IEEE, pp. 3185-3188 (Year: 2006).
Cooperative Multi-Scale Convolutional Neural, Networks for Person Detection, Markus Eisenbach, Daniel Seichter, Tim Wengefeld, and Horst-Michael Gross Ilmenau University of Technology, Neuroinformatics and Cognitive Robotics Lab (Year; 2016).
Chen, Yixin, James Ze Wang, and Robert Krovetz. "CLUE: cluster-based retrieval of images by unsupervised learning." IEEE transactions on Image Processing 14.8 (2005); 1187-1201. (Year: 2005).
Wusk et al (Non-Invasive detection of Respiration and Heart Rate with a Vehicle Seat Sensor; www.mdpi.com/journal/sensors; Published: May 8, 2018). (Year: 2018).
Chen, Tiffany Yu-Han, et al. "Glimpse: Continuous, real-time object recognition on mobile devices." Proceedings of the 13th ACM Confrecene on Embedded Networked Sensor Systems. 2015. (Year: 2015).
Zhou et al, "Ensembling neural networks: Many could be better than all", National Laboratory for Novel Software Technology, Nanjing University, Hankou Road 22, Nanjing 210093, PR China Received Nov. 16, 2001, Available online Mar. 12, 2002, pp. 239-263.
Zhou et al, "Medical Diagnosis With C4.5 Rule Preceded by Artificial Neural Network Ensemble", IEEE Transactions on Information Technology in Biomedicine, vol. 7, Issue: 1, Mar. 2003, pp. 37-42.
Zhu et al., "Technology-Assisted Dietary Assesment", Proc SPIE. Mar. 20, 2008, pp. 1-15.
Zou et al., "A Content-Based Image Authentication System with Lossless Data Hiding", ICME 2003, pp. 213-216.
"Computer Vision Demonstration Website", Electronics and Computer Science, University of Southampton, 2005, USA.
Big Bang Theory Series 04 Episode 12, aired Jan. 6, 2011; [retrieved from Internet: ].
Boari et al, "Adaptive Routing for Dynamic Applications in Massively Parallel Architectures", 1995 IEEE, Spring 1995, pp. 1-14.
Burgsteiner et al., "Movement Prediction from Real-World Images Using a Liquid State machine", Innovations in Applied Artificial Intelligence Lecture Notes in Computer Science, Lecture Notes in Artificial Intelligence, LNCS, Springer-Verlag, BE, vol. 3533, Jun. 2005, pp. 121-130.
Cernansky et al, "Feed-forward Echo State Networks", Proceedings of International Joint Conference on Neural Networks, Montreal, Canada, Jul. 31-Aug. 4, 2005, pp. 1-4.
Chinchor, Nancy A. et al.; Multimedia Analysis + Visual Analytics = Multimedia Analytics; IEEE Computer Society 2010; pp. 52-60. (Year: 2010).
Fathy et al, "A Parallel Design and Implementation For Backpropagation Neural Network Using MIMD Architecture", 8th Mediterranean Electrotechnical Conference, 19'96. MELECON '96, Date of Conference: May 13-16, 1996, vol. 3 pp. 1472-1475, vol. 3.
Freisleben et al, "Recognition of Fractal Images Using a Neural Network", Lecture Notes in Computer Science, 1993, vol. 6861, 1993, pp. 631-637.
Garcia, "Solving the Weighted Region Least Cost Path Problem Using Transputers", Naval Postgraduate School, Monterey, California, Dec. 1989.
Guo et al, AdOn: An Intelligent Overlay Video Advertising System (Year: 2009).
Hogue, "Tree Pattern Inference and Matching for Wrapper Induction on the World Wide Web", Master's Thesis, Massachusetts Institute of Technology, Jun. 2004, pp. 1-106.
Howlett et al, "A Multi-Computer Neural Network Architecture in a Virtual Sensor System Application", International journal of knowledge-based intelligent engineering systems, 4 (2). pp. 86-93, 133N 1327-2314.

Hua et al., "Robust Video Signature Based on Ordinal Measure", Image Processing, 2004, 2004 International Conference on Image Processing (ICIP), vol. 1, IEEE, pp. 685-688, 2004.
International Search Report and Written Opinion for PCT/US2016/050471, ISA/RU, Moscow, RU, dated May 4, 2017.
International Search Report and Written Opinion for PCT/US2016/054634, ISA/RU, Moscow, RU, dated Mar. 16, 2017.
International Search Report and Written Opinion for PCT/US2017/015831, ISA/RU, Moscow, RU, dated Apr. 20, 2017.
Johnson et al, "Pulse-Coupled Neural Nets: Translation, Rotation, Scale, Distortion, and Intensity Signal Invariance for Images", Applied Optics, vol. 33, No. 26, 1994, pp. 6239-6253.
Lau et al., "Semantic Web Service Adaptation Model for a Pervasive Learning Scenario", 2008 IEEE Conference on Innovative Technologies in Intelligent Systems and Industrial Applications, 2008, pp. 98-103.
Li et al ("Matching Commercial Clips from TV Streams Using a Unique, Robust and Compact Signature" 2005) (Year 2005).
Lin et al., "Generating robust digital signature for image/video authentication", Multimedia and Security Workshop at ACM Multimedia '98, Bristol, U.K., Sep. 1998, pp. 245-251.
Lu et al, "Structural Digital Signature for Image Authentication: An Incidental Distortion Resistant Scheme", IEEE Transactions on Multimedia, vol. 5, No. 2, Jun. 2003, pp. 161-173.
Lyon, "Computational Models of Neural Auditory Processing", IEEE International Conference on Acoustics, Speech, and Signal Processing, ICASSP '84, Date of Conference: Mar. 1984, vol. 9, pp. 41-44.
Ma Et El "Semantics modeling based image retrieval system using neural networks", 2005.
Marian Stewart B et al., "Independent component representations for face recognition", Proceedings of the SPIE Symposium on Electronic Imaging: Science and Technology; Conference on Human Vision and Electronic Imaging III, San Jose, California, Jan. 1998, pp. 1-12.
May et al, "The Transputer", Springer-Verlag Berlin Heidelberg 1989, vol. 41.
McNamara et al., "Diversity Decay in opportunistic Content Sharing Systems", 2011 IEEE International Symposium an a World of Wireless, Mobile and Multimedia Networks, pp. 1-3.
Morad et al., "Performance, Power Efficiency and Scalability of Asymmetric Cluster Chip Multiprocessors", Computer Architecture Letters, vol. 4, Jul. 4, 2005, pp. 1-4, XP002466254.
Nagy et al, "A Transputer, Based, Flexible, Real-Time Control System for Robotic Manipulators", UKACC International Conference on CONTROL '96, Sep. 2-5, 1996, Conference Publication No. 427, IEE 1996.
Natschlager et al., "The "Liquid Computer": A novel strategy for real-time computing on time series", Special Issue an Foundations of Information Processing of telematik, vol. 8, No. 1, 2002, pp. 39-43, XP002466253.
Odinaev et al, "Cliques in Neural Ensembles as Perception Carriers", Technion—Institute of Technology, 2006 International Joint Conference on neural Networks, Canada, 2006, pp. 285-292.
Ortiz-Boyer et al, "CIXL2: A Crossover Operator for Evolutionary Algorithms Based on Population Features", Journal of Artificial Intelligence Research 24 (2005) Submitted Nov. 2004; published Jul. 2005, pp. 1-48.
Pandya etal. A Survey on QR Codes: in context of Research and Application. International Journal of Emerging Technology and U Advanced Engineering. ISSN 2250-2459, ISO 9001:2008 Certified Journal, vol. 4, Issue 3, Mar. 2014 (Year: 2014).
Queluz, "Content-Based Integrity Protection of Digital Images", SPIE Conf. on Security and Watermarking of Multimedia Contents, San Jose, Jan. 1999, pp. 85-93.
Rui, Yong et al. "Relevance feedback: a power tool for interactive content-based image retrieval." IEEE Transactions an circuits and systems for video technology 8.5 (1998): 644-655.
Santos et al., "SCORM-MPEG: an Ontology of Interoperable Metadata for multimediaand E-Learning", 23rd International Conference on Software, Telecommunications and Computer Networks (SoftCom), 2015, pp. 224-228.

(56) References Cited

OTHER PUBLICATIONS

Scheper et al, "Nonlinear dynamics in neural computation", ESANN'2006 proceedings—European Symposium on Artificial Neural Networks, Bruges (Belgium), Apr. 26-28, 2006, d-side publication, ISBN 2-930307-06-4, pp. 1-12.

Schneider et al, "A Robust Content based Digital Signature for Image Authentication", Proc. ICIP 1996, Lausane, Switzerland, Oct. 1996, pp. 227-230.

Srihari et al., "Intelligent Indexing and Semantic Retrieval of Multimodal Documents", Kluwer Academic Publishers, May 2000, vol. 2, Issue 2-3, pp. 245-275.

Srihari, Rohini K. "Automatic indexing and content-based retrieval of captioned images" Computer 0 (1995): 49-56.

Stolberg et al ("HIBRID-SOC: a Multi-Core SOC Architecture for Multimedia Signal Processing" 2003).

Stolberg et al, "HIBRID-SOC: a Mul ti-Core SOC Architecture for Mul timedia Signal Processing", 2003 IEEE, pp. 189-194.

Theodoropoulos et al, "Simulating Asynchronous Architectures on Transputer Networks", Proceedings of the Fourth Euromicro Workshop on Parallel and Distributed Processing, 1996 PDP '96, pp. 274-281.

Vallet et al ("Personalized Content Retrieval in Context Using Ontological Knowledge" Mar. 2007) (Year: 2007).

Verstraeten et al, "Isolated word recognition with the Liquid State Machine: a case study", Department of Electronics and Information Systems, Ghent University, Sint-Pietersnieuwstraat 41, 9000 Gent, Belgium, Available onlline Jul. 14, 2005, pp. 521-528.

Wang et al., "Classifying Objectionable Websites Based onImage Content", Stanford University, pp. 1-12.

Ware et al, "Locating and Identifying Components in a Robot's Workspace using a Hybrid Computer Architecture" Proceedings of the 1995 IEEE International Symposium on Intelligent Control, Aug. 27-29, 1995, pp. 139-144.

Whitby-Strevens, "The transputer", 1985 IEEE, pp. 292-300.

Wilk et al., "The Potential of Social-Aware Multimedia Prefetching on Mobile Devices", International Conference and Workshops on networked Systems (NetSys), 2015, pp. 1-5.

Yanagawa et al, "Columbia University's Baseline Detectors for 374 LSCOM Semantic Visual Concepts", Columbia University ADVENT Technical Report # 222-2006-8, Mar. 20, 2007, pp. 1-17.

Yanagawa et al., "Columbia University's Baseline Detectors for 374 LSCOM Semantic Visual Concepts", Columbia University ADVENT Technical Report #222, 2007, pp. 2006-2008.

\* cited by examiner

Receiving information about a predicting pattern of a predicting physiological parameter, the predicting pattern has been found to predict an occurrence of a dangerous event 3110

Monitoring, by a monitor, a physiological state of a driver of the vehicle to provide physiological state information, and searching within the physiological state information for the predictive pattern 3120

Responding to the finding thereby reducing a change of a future occurrence of the dangerous event 3130

```
┌─────────────────────────────────────────────────────────────────────────┐
│ Determining which physiological parameters of one or more drivers of one or more vehicles should │
│ be monitored during a learning period. The determining may be executed in a random manner,       │
│ pseudo random manner, based on the capabilities of monitors (physiological monitors) that are    │
│ available for monitoring the one or more drivers 3202                                            │
└─────────────────────────────────────────────────────────────────────────┘
                                      ▼
┌─────────────────────────────────────────────────────────────────────────┐
│ Recording the, during one or more learning periods, the physiological parameters selected in step │
│ 3202. 3204                                                                                        │
└─────────────────────────────────────────────────────────────────────────┘
                                      ▼
┌─────────────────────────────────────────────────────────────────────────┐
│ Obtaining information regarding "dangerous events" cases that occurred during one or more         │
│ learning periods 3206                                                                             │
└─────────────────────────────────────────────────────────────────────────┘
                                      ▼
┌─────────────────────────────────────────────────────────────────────────┐
│ Breaking down the recording into random segments 3208                                             │
└─────────────────────────────────────────────────────────────────────────┘
                                      ▼
┌─────────────────────────────────────────────────────────────────────────┐
│ Building a baseline of parameters by statistically analyzing the parameters and comparing the     │
│ random events 3210                                                                                │
└─────────────────────────────────────────────────────────────────────────┘
                                      ▼
┌─────────────────────────────────────────────────────────────────────────┐
│ Obtaining the signal recording during an event. Cut random length segments before the event 3212 │
└─────────────────────────────────────────────────────────────────────────┘
                                      ▼
┌─────────────────────────────────────────────────────────────────────────┐
│ Performing statistical analysis of each segment and compare it to the baseline to Identify which  │
│ measurement changed 3214                                                                          │
└─────────────────────────────────────────────────────────────────────────┘
                                      ▼
┌─────────────────────────────────────────────────────────────────────────┐
│ Finding the earliest point when the measurement started changing. 3216                            │
└─────────────────────────────────────────────────────────────────────────┘
                                      ▼
┌─────────────────────────────────────────────────────────────────────────┐
│ Tracing later segments up to the event point to make sure that this measurement is indeed keep    │
│ changing up to the event point 3218                                                               │
└─────────────────────────────────────────────────────────────────────────┘

DRIVER-BASED PREDICTION OF DANGEROUS EVENTS

BACKGROUND

A physiological state of a driver may impact the manner in which a vehicle is driven by a driver. For example—many accidents resulted from a fatigued driver and/or a driver that was distracted for any other reason.

There is a growing need to predict a dangerous event based on the state of a driver.

SUMMARY

There may be provided a method for driver-based prediction of dangerous events, the method may include monitoring, by a monitor and during a learning period, a physiological state of a driver to provide physiological state information; wherein the physiological state information represents one or more physiological parameters of the driver; receiving or generating an indication about a dangerous event that occurred during the learning period; searching for a predicting physiological parameter of the one or more physiological parameters; wherein the predicting physiological parameter may be associated with a predicting pattern that was indicative of an occurrence of the dangerous event; and when finding the predicting physiological parameter then responding to the finding.

The predictive pattern may include (a) a change of the predicting physiological parameter within the leaning period and at a certain point in time before the occurrence of the dangerous event, and (b) maintaining the predicting physiological parameter, after the certain point in time, changed.

The finding of the predictive pattern may include comparing (a) statistics related to values of the predicting physiological parameter during at least a majority of the learning period, and (b) statistics related to values of the predicting physiological parameter at a part of the learning period that preceded the start of the dangerous event.

The at least majority may include the entire learning period.

The at least majority excludes a duration of the dangerous event.

The finding of the predictive pattern may include segmenting a part of the learning period to time segments; wherein the part of the learning period preceded the start of the dangerous event; calculating statistics related to values of the predicting physiological parameter during each time segment; and comparing (a) statistics related to values of the predicting physiological parameter during at least a majority of the learning period, and (b) the statistics related to values of the predicting physiological parameter during each of the time segments.

The time segments may be of random length.

The method may include monitoring, by multiple monitors, physiological states multiple drivers during multiple learning periods to provide physiological state information regarding the multiple drivers; wherein the physiological state information may be indicative of the one or more physiological parameters; receiving or generating indication about dangerous events that occurred during the multiple learning periods; searching for a predicting physiological parameter of the one or more physiological parameters; wherein each predicting physiological parameter may be associated with a predicting pattern that was indicative of an occurrence of one of the dangerous events; and when finding the predicting physiological parameter then responding to the finding.

The multiple drivers may be of a same gender.

The predicting physiological parameter may be selected out of a yawning rate, a blinking rate, an eyeballs movements rate, a parameter related to head turns, a direction of gaze, and one or more ECG parameters.

The responding may include instructing or requesting at least one monitor of at least one vehicle to monitor at least one driver of the at least one vehicle to search for a future occurrence of the predictive pattern in the predicting physiological parameter.

There may be provided a non-transitory computer readable medium that may store instructions for monitoring, by a monitor and during a learning period, a physiological state of a driver to provide physiological state information; wherein the physiological state information represents one or more physiological parameters of the driver; receiving or generating an indication about a dangerous event that occurred during the learning period; searching for a predicting physiological parameter of the one or more physiological parameters; wherein the predicting physiological parameter may be associated with a predicting pattern that was indicative of an occurrence of the dangerous event; and when finding the predicting physiological parameter then responding to the finding.

The predictive pattern may include (a) a change of the predicting physiological parameter within the leaning period and at a certain point in time before the occurrence of the dangerous event, and (b) maintaining the predicting physiological parameter, after the certain point in time, changed.

The finding of the predictive pattern may include comparing (a) statistics related to values of the predicting physiological parameter during at least a majority of the learning period, and (b) statistics related to values of the predicting physiological parameter at a part of the learning period that preceded the start of the dangerous event.

The at least majority may include the entire learning period.

The at least majority excludes a duration of the dangerous event.

The finding of the predictive pattern may include segmenting a part of the learning period to time segments; wherein the part of the learning period preceded the start of the dangerous event; calculating statistics related to values of the predicting physiological parameter during each time segment; and comparing (a) statistics related to values of the predicting physiological parameter during at least a majority of the learning period, and (b) the statistics related to values of the predicting physiological parameter during each of the time segments.

The time segments may be of random length.

The non-transitory computer readable medium may store instructions for monitoring, by multiple monitors, physiological states multiple drivers during multiple learning periods to provide physiological state information regarding the multiple drivers; wherein the physiological state information may be indicative of the one or more physiological parameters; receiving or generating indication about dangerous events that occurred during the multiple learning periods; searching for a predicting physiological parameter of the one or more physiological parameters; wherein each predicting physiological parameter may be associated with a predicting pattern that was indicative of an occurrence of one of the dangerous events; and when finding the predicting physiological parameter then instructing or requesting at least one monitor to monitor at least one driver of at least one vehicle to search for the predicting pattern.

The multiple drivers may be of a same gender.

The predicting physiological parameter may be selected out of a yawning rate, a blinking rate, an eyeballs movements rate, a parameter related to head turns, a direction of gaze, and one or more ECG parameters.

There may be provided a method for predicting an occurrence of a dangerous event, the method may include receiving information about a predicting pattern of a predicting physiological parameter, the predicting pattern has been found to predict an occurrence of a dangerous event; monitoring, by a monitor, a physiological state of a driver of the vehicle to provide physiological state information, and searching within the physiological state information for the predictive pattern; following a finding of the predictive pattern, responding to the finding thereby reducing a change of a future occurrence of the dangerous event.

BRIEF DESCRIPTION OF THE DRAWINGS

The embodiments of the disclosure will be understood and appreciated more fully from the following detailed description, taken in conjunction with the drawings in which:

FIGS. 1-3 illustrate examples of methods;

DESCRIPTION OF EXAMPLE EMBODIMENTS

Figure 1:
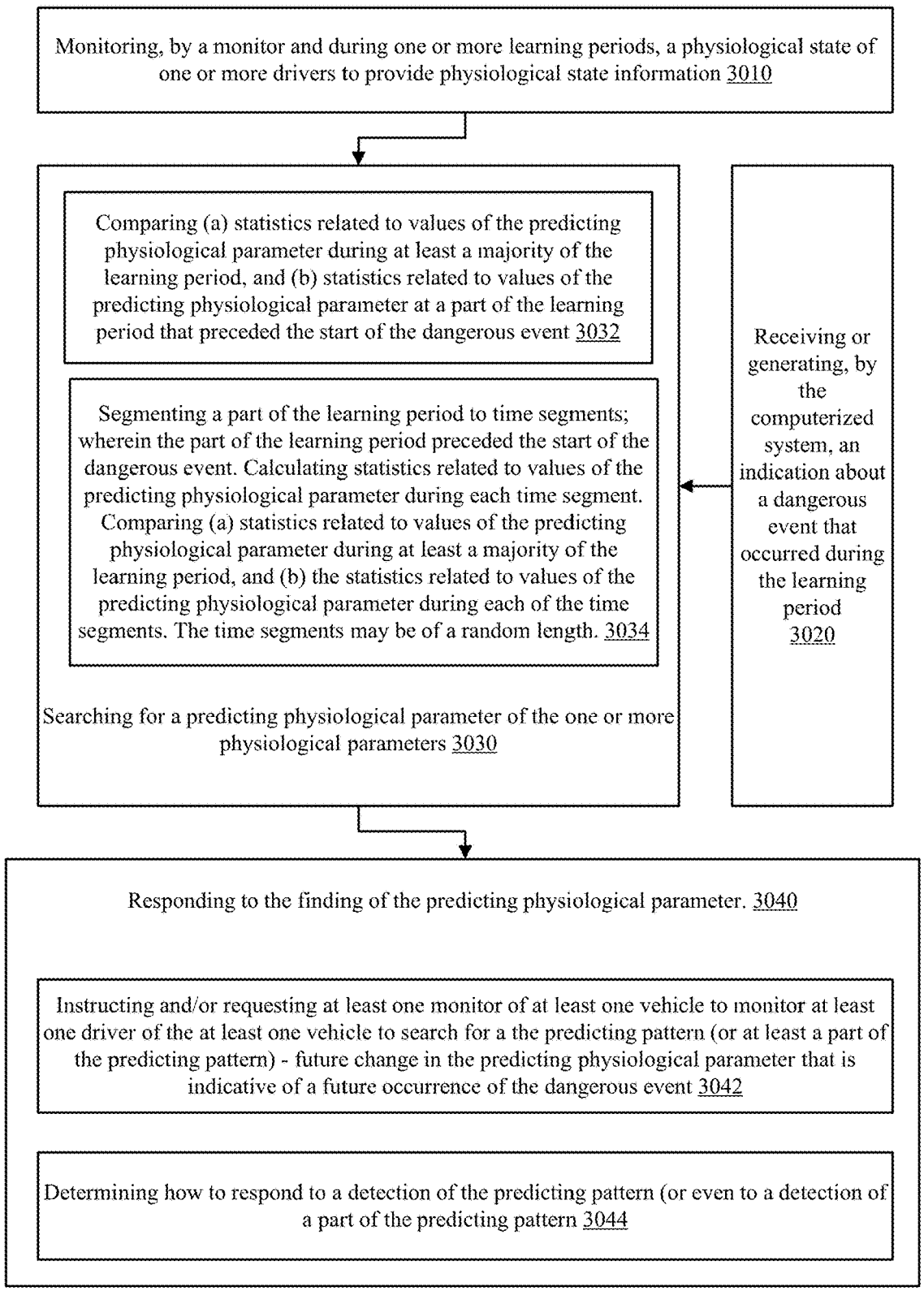

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a device or system capable of executing the method and/or to a non-transitory computer readable medium that stores instructions for executing the method.

Any reference in the specification to a system or device should be applied mutatis mutandis to a method that may be executed by the system, and/or may be applied mutatis mutandis to non-transitory computer readable medium that stores instructions executable by the system.

Any reference in the specification to a non-transitory computer readable medium should be applied mutatis mutandis to a device or system capable of executing instructions stored in the non-transitory computer readable medium and/or may be applied mutatis mutandis to a method for executing the instructions.

Any combination of any module or unit listed in any of the figures, any part of the specification and/or any claims may be provided.

A dangerous event is an event during which a vehicle was damaged, the vehicle caused damage to another party, a near miss, or any other behavior that was defines as a dangerous event. For example—an acceleration (positive or negative) within a prohibited or unwanted acceleration range, a speed that is within a prohibited or unwanted speed range, sharp change of direction and/or speed and/or rotation, sudden and significant breaks and the like.

A near miss, "near hit", "close call", or "nearly a collision" is defined in www.wikipedia.org as an unplanned event that has the potential to cause, but does not actually result in human injury, environmental or equipment damage, or an interruption to normal operation.

There may be provided a system, method and non-transitory computer readable medium that may automatically, especially in an unsupervised manner detect one or more physiological parameters of a driver that may predict a future dangerous events. The one or more physiological parameters may be found by analyzing one or more physiological parameters or one or more drivers that were acquired before an occurrence of dangerous events—and finding changes in the values of the one or more physiological parameters that precede the occurrence of dangerous events and are characteristic of a future occurrence of dangerous events.

During a learning period, the method may receive or generate an indication regarding an occurrence of one or more dangerous event and search in an unsupervised manner, within a vast amount of physiological state information gained from one or many drivers, predicting patterns of predicting physiological parameter that were indicative of the one or more dangerous event. The unsupervised learning and the potential access to vast amount of physiological state information may find predicting patterns—even if these predicting patterns are not expected, may be performed without previous assumptions (without limiting, unnecessarily, the scope of the search), and may provide highly accurate predicting patterns.

It should be noted that a predicting pattern may include combination of patterns of physiological parameters. Accordingly—any reference to a predicting pattern should be applied to a predicting pattern of a single physiological parameter and/or to a combination of patterns of physiological parameters.

FIG. 1 illustrate method 3000.

Method 3000 may be applied by a computerized system that is a remote computerized system (not located in a vehicle) or a computerized system located in one or more vehicle. For example—multiple vehicle computers located within multiple vehicles can participate in the execution of the method.

Method 3000 may start by step 3010 of monitoring, by a monitor and during one or more learning periods, a physiological state of one or more drivers to provide physiological state information. The physiological state information related to a driver represents one or more physiological parameters of the driver.

The one or more learning periods may be of any duration.

The monitor may directly or indirectly measure the one or more physiological parameters. A direct monitoring of a physiological parameter may involve measuring the physiological parameter by the monitor. An indirect monitoring of a certain physiological parameter may include measuring another physiological parameter and inferring the certain physiological parameter from the other physiological parameter. For example—stress may be inferred from a blood pressure of the driver.

The monitor may be attached to the driver, may be spaced apart from the driver, may be installed in a driving wheel, may be coupled to the driving wheel, may be installed in a driver seat (for example—embedded under the fabric of the driver seat), may be coupled to the driver seat, may be installed in the vehicle, may be detachably connected to the vehicle, may be worn by the driver, may be a dedicated health monitor, may be a smartphone, may be included in a wrist band, may be a radar, may be a temperature sensor, may be a camera (visual light, wideband camera, narrow band camera, RBG (red, blue and green) camera, near infrared camera, infrared camera), may be a motion sensor, may be a stress sensor, may be an electrocardiography (EKG) sensor, may be an Electroencephalography (EEG) sensor, may be an ultrasonic sensor, may be a sonar, may be an acoustic sensor, and the like.

The one or more physiological parameters may be any physiological parameter. Non-limiting examples may include any parameter related to ECG parameters (PR interval, ST Interval, RR interval), EEG parameter, heartbeat, blood pressure, sweat, breathing rate, yawning rate, blinking rate, eyeballs movements rate, head turns, changes of direction of gaze, direction of gaze, and the like.

Method 3000 may also include step 3020 of receiving or generating, by the computerized system, an indication about a dangerous event that occurred during the learning period.

Steps 3010 and 3020 may be followed by step 3030 of searching for a predicting physiological parameter of the one or more physiological parameters.

The predicting physiological parameter is a physiological parameter that may be used to predict a dangerous event.

One or more physiological parameters may predict one or more dangerous events. Thus—a single predicting physiological parameter may predict different dangerous events, a single predicting physiological parameter may predict only one dangerous event, multiple predicting physiological parameters may predict different dangerous events, or multiple predicting physiological parameters may predict only one dangerous event.

For simplicity of explanation it is assumed that one physiological parameter is used to predict a single dangerous event.

The predicting physiological parameter is a physiological parameter that may have a predicting pattern—a pattern that is indicative of the dangerous event. For example—the pattern may include a change in the physiological parameter (measured within the leaning period) at a certain point in time before the occurrence of the dangerous event. The change may be followed by having the physiological parameter maintained changed until the occurrence of the dangerous event.

The certain point of time may be, for example, few seconds or few minutes before the occurrence of the dangerous event.

Any of the methods listed in the specification may generate statistical information regarding the time period between the beginning of a predicting pattern and a time of the occurrence of the dangerous event that is predicted by the predicting pattern.

The time difference between the certain point in time and the time of occurrence of the dangerous event should be long enough to enable to respond to the change in the predicting physiological parameter—but may be short enough as not to nullify the causal relationship between the predicting physiological parameter and the dangerous event.

The searching after the predicting physiological parameter may include determining a time of occurrence of the dangerous event and analyzing patterns of physiological parameters that preceded the time of occurrence of the dangerous event and may be indicative of the dangerous events.

Step 3030 may include at least step of steps 3032 and 3034.

Step 3032 may include comparing (a) statistics related to values of the predicting physiological parameter during at least a majority of the learning period, and (b) statistics related to values of the predicting physiological parameter at a part of the learning period that preceded the start of the dangerous event.

The comparison may provide an indication of the predicting pattern—especially of a change of the predicting physiological parameter that may be indicative of the occurrence of the dangerous event.

The at least majority may include the entire learning period.

The at least majority may exclude or include a duration of the dangerous event.

Step 3034 may include:
a. Segmenting a part of the learning period to time segments; wherein the part of the learning period preceded the start of the dangerous event.
b. Calculating statistics related to values of the predicting physiological parameter during each time segment.
c. Comparing (a) statistics related to values of the predicting physiological parameter during at least a majority of the learning period, and (b) the statistics related to values of the predicting physiological parameter during each of the time segments. The time segments may be of a random length.

Assuming that step 3030 found a predicting physiological parameter (and a predicting pattern of the predicting physiological parameter)—then step 3030 may be followed by step 3040 of responding to the finding of the predicting physiological parameter.

Step 3040 may include step 3042 of instructing and/or requesting at least one monitor of at least one vehicle to monitor at least one driver of the at least one vehicle to search for a predicting pattern (or at least a part of the predicting pattern)—future change in the predicting physiological parameter that is indicative of a future occurrence of the dangerous event.

Step 3040 may include step 3044 of determining how to respond to a detection of the predicting pattern (or even to a detection of a part of the predicting pattern). The response is aimed to reduce the occurrence of a future dangerous event. The response may include at least one out of alerting the driver, alerting another person in the vehicle, changing a behavior of the vehicle, handling a control over the vehicle to an a autonomic system, reducing the velocity of the vehicle, generating an alert that can be seen by other drivers and/or other vehicle nearby (to alert them that the driver handles the vehicle in a dangerous manner), alerting the police, slowing down the vehicle shutting down the vehicle, driving the vehicle to predefined safe locations (such as parking lots), parking the vehicle, venting the vehicle with fresh air, and the like.

The response may include at least one out of requesting, instructing or otherwise triggering another system, and/or entity and/or unit to perform at least one of the following: alerting the driver, alerting another person in the vehicle, changing a behavior of the vehicle, handling a control over the vehicle to an a autonomic system, reducing the velocity of the vehicle, generating an alert that can be seen by other drivers and/or other vehicle nearby (to alert them that the driver handles the vehicle in a dangerous manner), alerting the police, slowing down the vehicle shutting down the vehicle, driving the vehicle to predefined safe locations (such as parking lots), parking the vehicle, venting the vehicle with fresh air, and the like.

The determination may be based on monitored drivers that undergone the same driving conditions as a driver that undergone an dangerous event—but managed to escape the dangerous event. For example—is an accident occurred due to a slippery road segment—but other drivers passes the slippery road segment harmless—then the behavior of the other drivers may provide a basis for how to avoid the dangerous event.

Step 3040 may include requesting at least one monitor of at least one vehicle to monitor at least one driver of the at least one vehicle to search for a future change in the predicting physiological parameter that is indicative of a future occurrence of the dangerous event.

Step 3040 may include adapting the predicting pattern to other drivers. This may include normalizing the predicting pattern, and adapting the normalized pattern to baselines of other drivers.

Step 3040 may include distributing information regarding the predicting physiological parameter—especially information about the predicting pattern to other vehicles, other monitors, and the like.

FIG. 2 illustrates method 3100 for predicting an occurrence of a dangerous event.

Method 3100 may start by step 3110 of receiving information about a predicting pattern of a predicting physiological parameter, the predicting pattern has been found to predict an occurrence of a dangerous event. The information about the predicting pattern of the predicting physiological parameter may be generated by executing method 3000.

Step 3110 may be followed by step 3120 of monitoring, by a monitor, a physiological state of a driver of the vehicle to provide physiological state information, and searching within the physiological state information for the predictive pattern.

When finding the predictive pattern—then step 3120 may be followed by step 3130 of responding to the finding thereby reducing a change of a future occurrence of the dangerous event.

The responding may include at least one out of alerting the driver, alerting another person in the vehicle, changing a behavior of the vehicle, handling a control over the vehicle to an a autonomic system, reducing the velocity of the vehicle, generating an alert that can be seen by other drivers and/or other vehicle nearby (to alert them that the driver handles the vehicle in a dangerous manner), alerting the police, slowing down the vehicle shutting down the vehicle, driving the vehicle to predefined safe locations (such as parking lots), parking the vehicle, venting the vehicle with fresh air, and the like.

The responding may include at least one out of requesting, instructing or otherwise triggering another system, and/or entity and/or unit to perform at least one of the following: alerting the driver, alerting another person in the vehicle, changing a behavior of the vehicle, handling a control over the vehicle to an a autonomic system, reducing the velocity of the vehicle, generating an alert that can be seen by other drivers and/or other vehicle nearby (to alert them that the driver handles the vehicle in a dangerous manner), alerting the police, slowing down the vehicle shutting down the vehicle, driving the vehicle to predefined safe locations (such as parking lots), parking the vehicle, venting the vehicle with fresh air, and the like.

It should be noted that method 3100 may be executed by an autonomous vehicle, by a partially autonomous vehicle or by a non-autonomous vehicle. In case of a partially autonomous vehicle or by a non-autonomous vehicle some of the mentioned above responses (that require an autonomous vehicle) will not be executed.

FIG. 3 illustrates method 3200.

Method 3200 may include the following steps:

a. Step 3202 of determining which physiological parameters of one or more drivers of one or more vehicles should be monitored during a learning period. The determining may be executed in a random manner, pseudo random manner, based on the capabilities of monitors (physiological monitors) that are available for monitoring the one or more drivers.

b. Step 3204 of recording the, during one or more learning periods, the physiological parameters selected in step 3202.

c. Step 3206 of obtaining information regarding "dangerous events" cases that occurred during one or more learning periods. This may involve measuring or receiving telematic parameters, measuring or receiving visual information, manually tagging events as dangerous, receiving from a party outside the vehicle an indication of a dangerous event, and the like.

d. Step 3208 of breaking down the recording into random segments. For each segment measure the behavior/value of each measurement in this random segment (heart rate, oxygen level, yawning rate, blinking rate, eyeballs movements rate, head turns, looking away, eyes down etc). For example—it may be expected that an increase in the blinking rate may be indicative of tiredness, that an increase of the pupils may be indicative of tiredness.

e. Step 3210 of building a baseline of parameters by statistically analyzing the parameters and comparing the random events. The baseline can be (i) general population, (ii) broken down per group (e.g male vs female)—again by unsupervised clustering, or supervised by obtaining driver's metadata, (iii) personalized per driver (the most accurate approach).

f. Step 3212 of obtaining the signal recording during an event. Cut random length segments before the event.

g. Step 3214 of performing statistical analysis of each segment and compare it to the baseline to Identify which measurement changed.

h. Step 3216 of finding the earliest point when the measurement started changing.

i. Step 3218 of tracing later segments up to the event point to make sure that this measurement is indeed keep changing up to the event point (and not some random not related change like someone told a joke on the phone and laugh rate and heart rate increased temporarily).

Any combination of any steps of any one or methods 3000, 3100 and 3200 may be provided.

Figure 4:
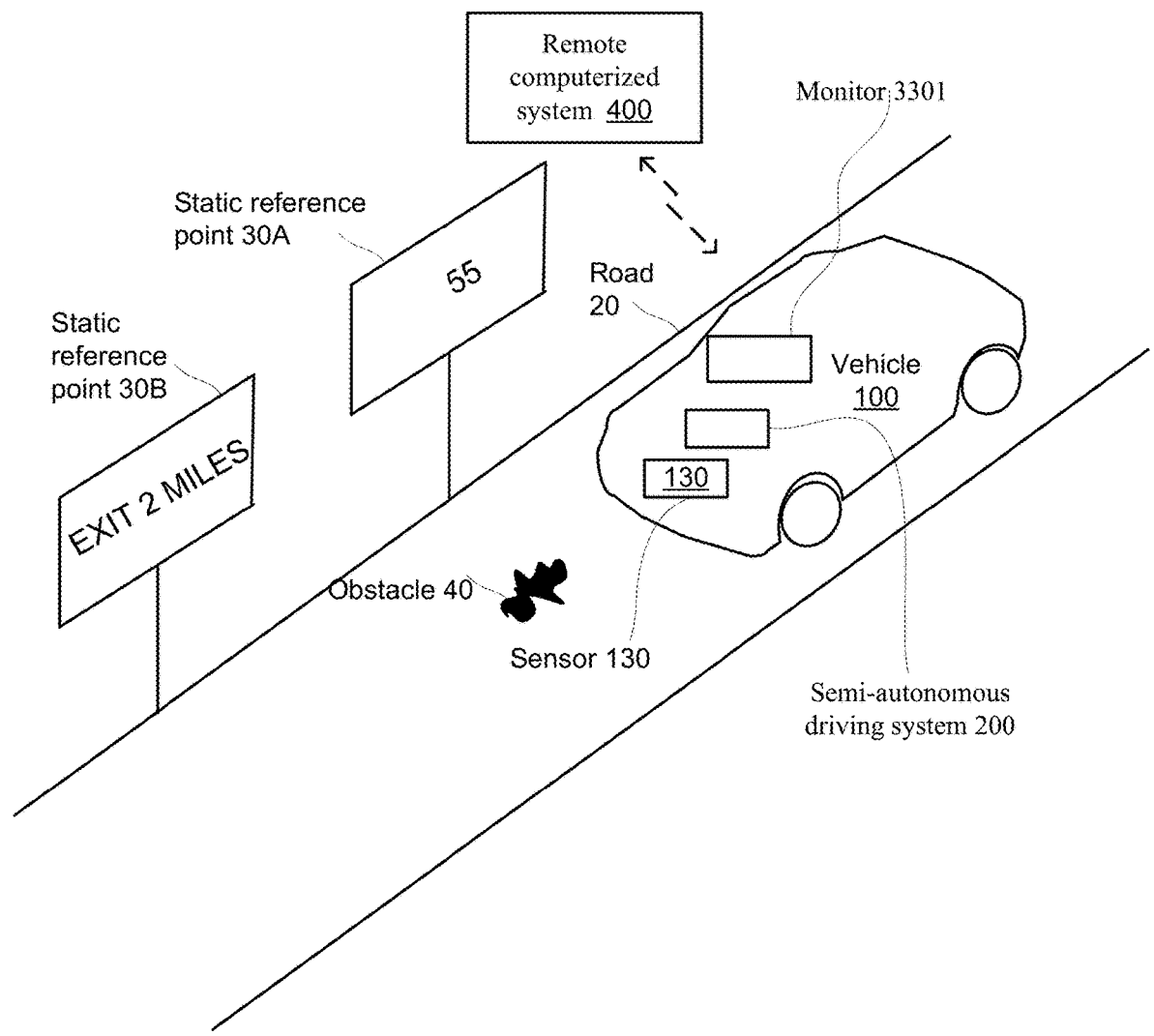
FIG. 4 is a partly-pictorial, partly-block diagram illustration of an exemplary obstacle detection and mapping system, constructed and operative in accordance with embodiments described herein.

Reference is now made to FIG. 4, which is a partly-pictorial, partly-block diagram illustration of an exemplary system 10 constructed and operative in accordance with embodiments described herein.

System 10 comprises vehicle 100 and a remote computerized system such as remote computerized system 400 which may be configured to communicate with each other over a communications network such as, for example, the Internet.

In accordance with the exemplary embodiment of FIG. 4, vehicle 100 may be configured with a semi-autonomous driving system 200 (or "semi-autonomous") driving system where in at least some situations a human driver may take control of vehicle 100 and/or where in at least some situations the semi-autonomous driving system provides warnings to the driver without necessarily directly controlling vehicle 100.

Remote system 400 may execute method 3000 and/or method 3200. Vehicle 10 may execute method 3000 and/or method 3100 and/or method 3200.

In accordance with the exemplary embodiment of FIG. 4, vehicle 100 may be configured with at least one sensor 130 to provide information about a current driving environment as vehicle 100 proceeds along roadway 20. The vehicle or the user may be equipped by one or more physiological sensors that may belong to monitor 3301.

Monitor 3301 may be configured to monitor a physiological state of a driver of the vehicle to provide physiological state information.

Monitor 3301 may be also configured to (a) receive information about a predicting pattern of a predicting physiological parameter, the predicting pattern has been found to predict an occurrence of a dangerous event, and to search within the physiological state information (generated by monitor 3301) for the predictive pattern.

It will be appreciated that while sensor 130 is depicted in FIG. 4 as a single entity, in practice, as will be described hereinbelow, there may be multiple sensors 130 arrayed on, or inside of, vehicle 130. The same applied to monitor 3301 and the physiological sensors 3303.

In accordance with embodiments described herein, sensor (s) 130 may be implemented using a conventional camera operative to capture images of roadway 20 and objects in its immediate vicinity. It will be appreciated that sensor 130 may be implemented using any suitable imaging technology instead of, or in addition to, a conventional camera. For example, sensor 130 may also be operative to use infrared, radar imagery, ultrasound, electro-optics, radiography, LIDAR (light detection and ranging), etc. Furthermore, in accordance with some embodiments, one or more sensors 130 may also be installed independently along roadway 20, where information from such sensors 130 may be provided to vehicle 100 and/or computerized system 400 as a service.

In accordance with the exemplary embodiment of FIG. 4, static reference points 30A and 30B (collectively referred to hereinafter as static reference points 30) may be located along roadway 20. For example, static reference point 30A is depicted as a speed limit sign, and static reference point 30B is depicted as an exit sign. In operation, sensor 130 may capture images of static reference points 30. The images may then be processed by the autonomous driving system in vehicle 100 to provide information about the current driving environment for vehicle 100, e.g., the speed limit or the location of an upcoming exit.

Figure 5:
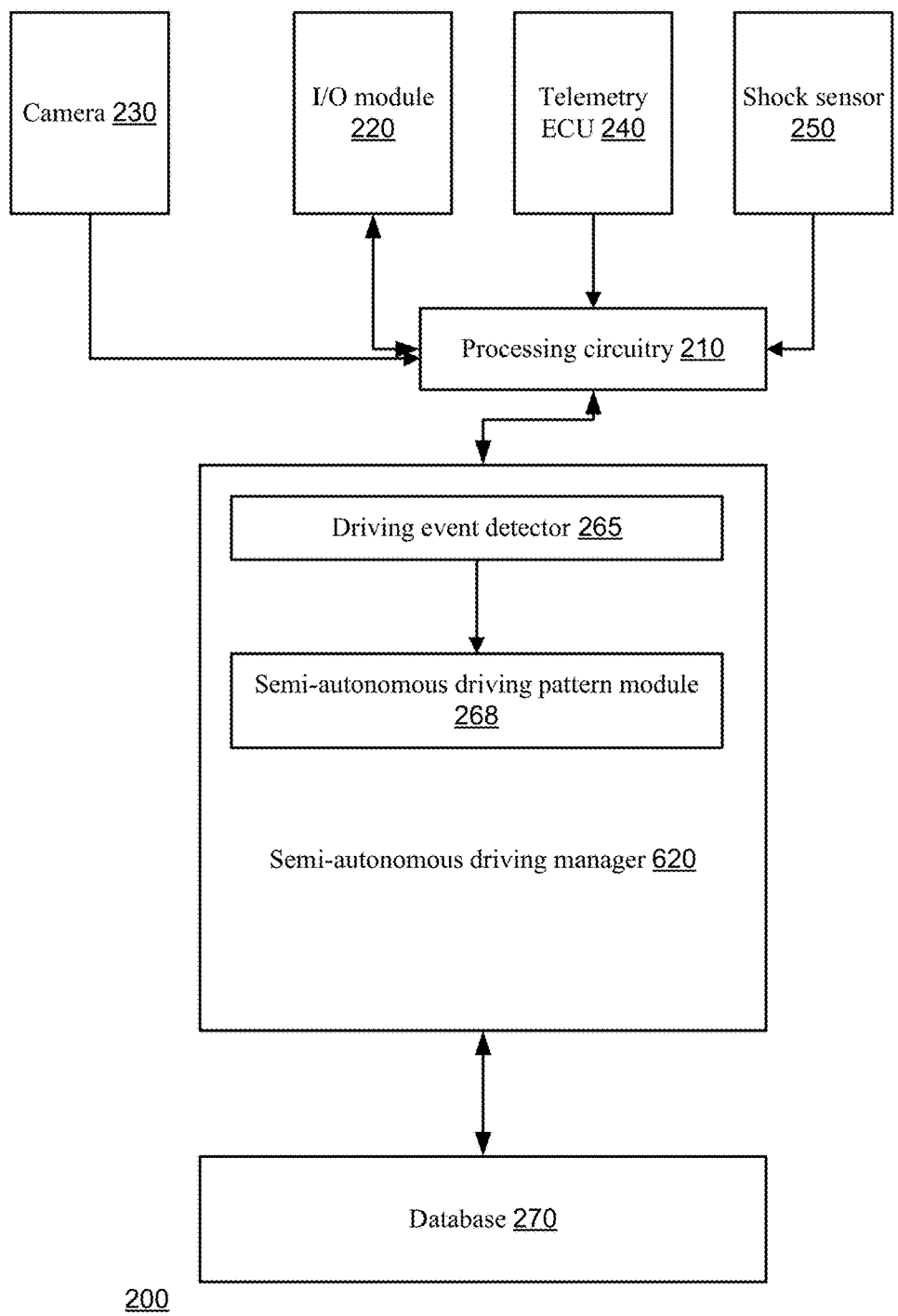
FIG. 5 is a block diagram of an exemplary autonomous driving system to be integrated in the vehicle of FIG. 4.

Reference is now made to FIG. 5 which is a block diagram of an exemplary semi-autonomous driving system 200 (hereinafter also referred to as system 200), constructed and implemented in accordance with embodiments described herein.

System 200 may receive information from monitor 3301. The system 200 may participate in responding to a detection of a predicting pattern (indicative of a future occurrence of a dangerous event) that was found by the monitor.

System 200 comprises processing circuitry 210, input/output (I/O) module 220, camera 230, telemetry ECU 240, shock sensor 250, semi-autonomous driving manager 260, and database 270. The semi-autonomous driving manager 260 may be used for assisting the driver and/or may be used for autonomously driving the vehicle during certain periods and for handing over the control of the vehicle to the driver at other periods.

Semi-autonomous driving manager 260 may be instantiated in a suitable memory for storing software such as, for example, an optical storage medium, a magnetic storage medium, an electronic storage medium, and/or a combination thereof. It will be appreciated that system 200 may be implemented as an integrated component of an onboard computer system in a vehicle, such as, for example, vehicle 100 from FIG. 4. Alternatively, system 200 may be implemented and a separate component in communication with the onboard computer system. It will also be appreciated that in the interests of clarity, while system 200 may comprise additional components and/or functionality e.g., for semi-autonomous driving of vehicle 100, such additional components and/or functionality are not depicted in FIG. 2 and/or described herein.

Processing circuitry 210 may be operative to execute instructions stored in memory (not shown). For example, processing circuitry 210 may be operative to execute semi-autonomous driving manager 260. It will be appreciated that processing circuitry 210 may be implemented as a central processing unit (CPU), and/or one or more other integrated circuits such as application-specific integrated circuits (ASICs), field programmable gate arrays (FPGAs), full-custom integrated circuits, etc., or a combination of such integrated circuits. It will similarly be appreciated that system 200 may comprise more than one instance of processing circuitry 210. For example, one such instance of processing circuitry 210 may be a special purpose processor operative to execute autonomous driving manager 260 to perform some, or all, of the functionality of system 200 as described herein.

I/O module 220 may be any suitable communications component such as a network interface card, universal serial bus (USB) port, disk reader, modem or transceiver that may be operative to use protocols such as are known in the art to communicate either directly, or indirectly, with other elements of system 10 (FIG. 1) and/or system 200, such as, for example, computerized system 400 (FIG. 4), camera 230, telemetry ECU 240, and/or shock sensor 250. As such, I/O module 220 may be operative to use a wired or wireless connection to connect to computerized system 400 via a communications network such as a local area network, a backbone network and/or the Internet, etc. I/O module 220 may also be operative to use a wired or wireless connection to connect to other components of system 200, e.g., camera 230, telemetry ECU 240, and/or shock sensor 250. It will be appreciated that in operation I/O module 220 may be implemented as a multiplicity of modules, where different modules may be operative to use different communication technologies. For example, a module providing mobile network connectivity may be used to connect to computerized system 400, whereas a local area wired connection may be used to connect to camera 230, telemetry ECU 240, and/or shock sensor 250.

In accordance with embodiments described herein, camera 230, telemetry ECU 240, and shock sensor 250 represent implementations of sensor(s) 130 from FIG. 4. It will be appreciated that camera 230, telemetry ECU 240, and/or shock sensor 250 may be implemented as integrated components of vehicle 100 (FIG. 4) and may provide other functionality that is the interests of clarity is not explicitly described herein. As described hereinbelow, system 200 may use information about a current driving environment as received from camera 230, telemetry ECU 240, and/or shock sensor 250 to determine an appropriate driving policy for vehicle 100.

Semi-autonomous driving manager 260 may be an application implemented in hardware, firmware, or software that may be executed by processing circuitry 210 to provide driving instructions to vehicle 100. For example, semi-autonomous driving manager 260 may use images received from camera 230 and/or telemetry data received from telemetry ECU 240 to determine an appropriate driving policy for arriving at a given destination and provide driving instructions to vehicle 100 accordingly. It will be appreciated that semi-autonomous driving manager 260 may also be operative to use other data sources when determining a driving policy, e.g., maps of potential routes, traffic congestion reports, etc.

As depicted in FIG. 5, semi-autonomous driving manager 260 comprises driving event detector 265 and semi-autonomous driving pattern module 268. It will be appreciated that the depiction of driving event detector 265 and semi-autonomous driving pattern module 268 as integrated components of semi-autonomous driving manager 260 may be exemplary. The embodiments described herein may also support implementation of driving event detector 265 and semi-autonomous driving pattern module 268 as independent applications in communication with semi-autonomous driving manager 260, e.g., via I/O module 220.

Driving event detector 265 and semi-autonomous driving pattern module 268 may be implemented in hardware, firmware, or software and may be invoked by semi-autonomous driving manager 260 as necessary to provide input to the determination of an appropriate driving policy for vehicle 100.

Depending on the configuration of system 100, the information from computerized system 400 may be received in a batch update process, either periodically and/or triggered by an driving event, e.g., when vehicle 100 is turned on, when vehicle 100 enters a new map area, when vehicle 100 enters an area with good wireless reception, etc.

Figure 6:
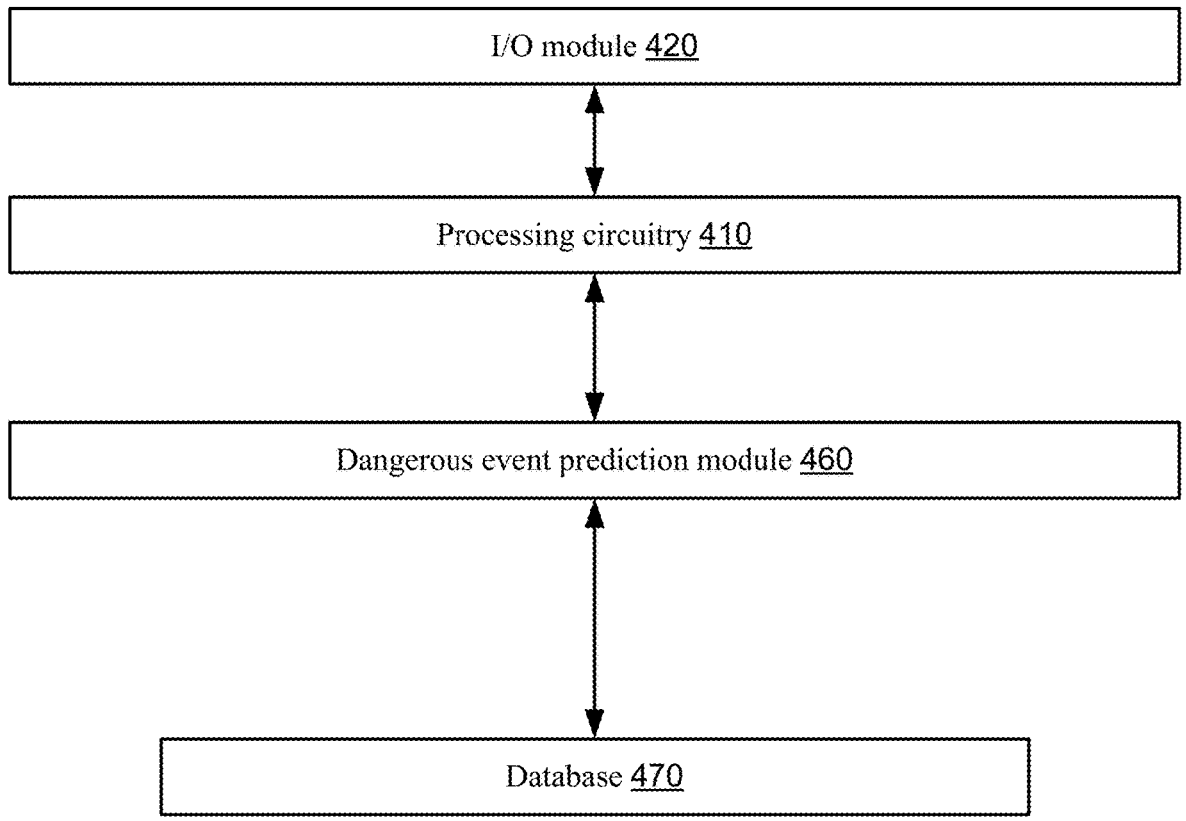
FIG. 6 is a block diagram of an computerized system.

Reference is now made to FIG. 6 which is a block diagram of a computerized system 400 (hereinafter also referred to as computerized system 400), constructed and implemented in accordance with embodiments described herein.

Computerized system 400 comprises processing circuitry 410, input/output (I/O) module 420, dangerous event prediction module 460, and database 470. The dangerous event prediction module may be instantiated in a suitable memory for storing software such as, for example, an optical storage medium, a magnetic storage medium, an electronic storage medium, and/or a combination thereof.

Processing circuitry 410 may be operative to execute instructions stored in memory (not shown). For example, processing circuitry 410 may be operative to execute dangerous event prediction module 460. It will be appreciated that processing circuitry 410 may be implemented as a central processing unit (CPU), and/or one or more other integrated circuits such as application-specific integrated circuits (ASICs), field programmable gate arrays (FPGAs), full-custom integrated circuits, etc., or a combination of such integrated circuits. It will similarly be appreciated that computerized system 400 may comprise more than one instance of processing circuitry 410. For example, one such instance of processing circuitry 410 may be a special purpose processor operative to execute the dangerous event prediction module 460 to perform some, or all, of the functionality of computerized system 400 as described herein.

I/O module 420 may be any suitable communications component such as a network interface card, universal serial bus (USB) port, disk reader, modem or transceiver that may be operative to use protocols such as are known in the art to communicate either directly, or indirectly, with other elements of system 10 (FIG. 4) such as, for example, system 200 (FIG. 5). As such, I/O module 420 may be operative to use a wired or wireless connection to connect to system 200 via a communications network such as a local area network, a backbone network and/or the Internet, etc. It will be appreciated that in operation I/O module 220 may be implemented as a multiplicity of modules, where different modules may be operative to use different communication technologies. For example, a module providing mobile network connectivity may be used to connect wirelessly to one instance of system 200, e.g., one vehicle 100 (FIG. 4), whereas a local area wired connection may be used to connect to a different instance of system 100, e.g., a different vehicle 100.

Dangerous event prediction module 460 may be an application implemented in hardware, firmware, or software that may be executed by processing circuitry 410 to provide driving event identifiers and tailored comfort based autonomous driving pattern information for each one of the multiple types of driving events.

Figure 7:
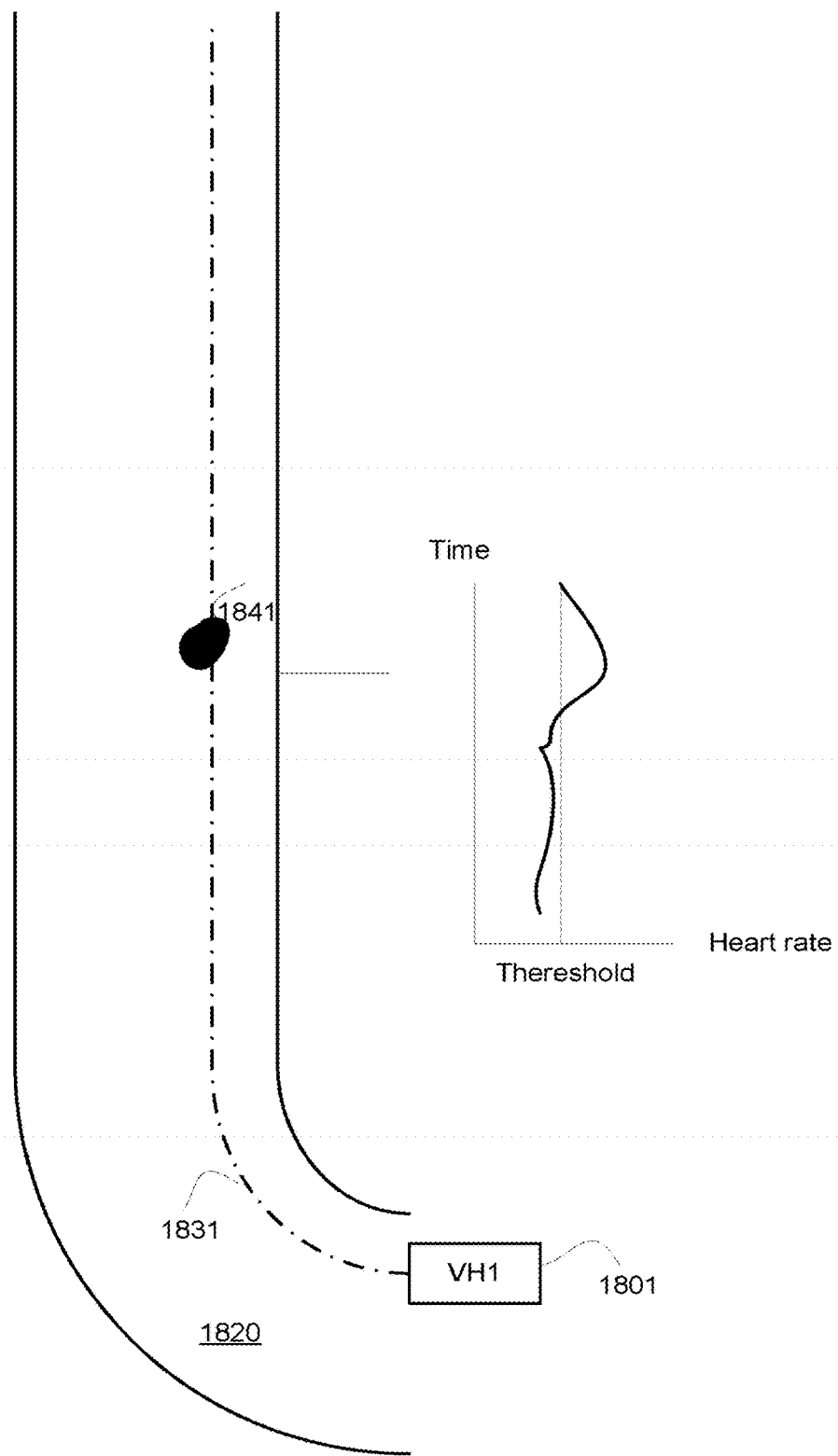
FIGS. 7-8 illustrate various examples of dangerous events.
Figure 8:
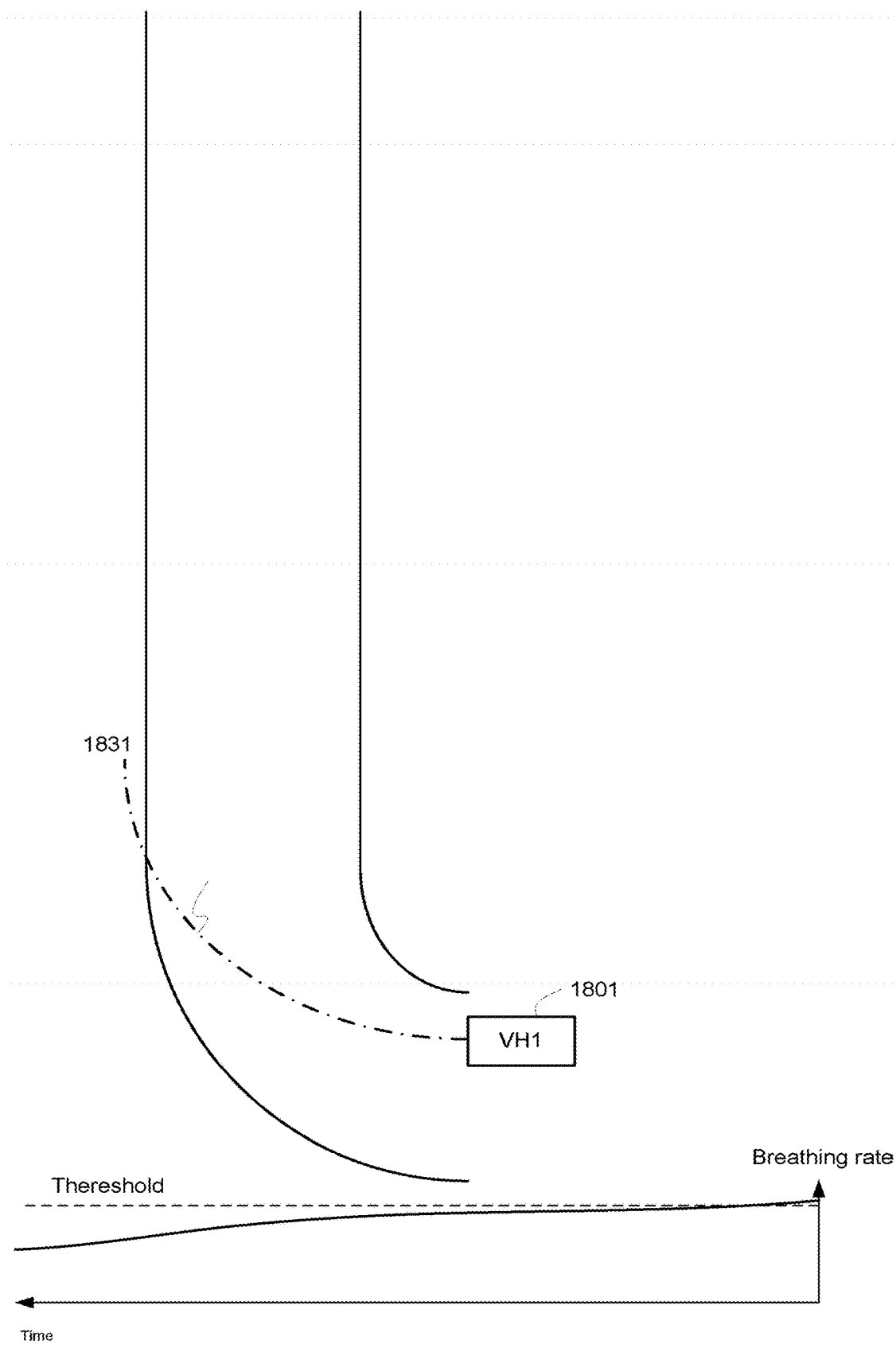

Each one of FIGS. 7-8 may illustrate a dangerous events that occurred during a learning period and/or dangerous events that may be predicted in advance—and be avoided using methods 3100 or 3200.

It is assumed, for sake of brevity, the these figures relate to a learning period.

FIG. 7 illustrates a first vehicle (VH1) 1801 that propagates along a road 1820.

The heartbeat of the driver increases (exhibits a predicting pattern)—and exceeds a threshold (or exhibit a change rate that exceeds a threshold) before reaching an obstacle 1841—assuming that the driving over the obstacle is considered as a dangerous event—then the increased heart rate may predict a future crossing of the obstacle.

FIG. 8 illustrates a first vehicle (VH1) 1801 that propagates along a road 1820 and misses a turn—thereby crossing an opposite lane and driving out of the road (see curve 1831).

The breathing rate of the driver decreases (exhibits a predicting pattern)—and is below a threshold (or exhibit a change rate that exceeds a threshold) well before reaching the turn—assuming that curve 1831 represents a dangerous event—then the decreased breathing rate may predict a future deviation from the road.

In any of the methods any of the autonomous driving pattern related to The driving event may be amended based on feedback provided by users of the vehicle.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It is appreciated that various features of the embodiments of the disclosure which are, for clarity, described in the contexts of separate embodiments may also be provided in combination in a single embodiment. Conversely, various features of the embodiments of the disclosure which are, for brevity, described in the context of a single embodiment may also be provided separately or in any suitable sub-combination.

It will be appreciated by persons skilled in the art that the embodiments of the disclosure are not limited by what has been particularly shown and described hereinabove. Rather the scope of the embodiments of the disclosure is defined by the appended claims and equivalents thereof.

What is claimed is:

1. A method for driver-based prediction of dangerous events, the method comprises:
monitoring, by a monitor and during a learning period, a physiological state of a driver to provide physiological state information; wherein the physiological state information represents one or more physiological parameters of the driver;
receiving or generating an indication about a dangerous event that occurred during the learning period;
searching for a predicting physiological parameter of the one or more physiological parameters; wherein the predicting physiological parameter is associated with a predicting pattern that was indicative of an occurrence of the dangerous event; and when finding the predicting physiological parameter then responding to the finding;

wherein the predictive pattern comprises (a) a change of the predicting physiological parameter within the learning period and at a certain point in time before the occurrence of the dangerous event, and (b) maintaining the predicting physiological parameter, after the certain point in time, changed.

2. The method according to claim 1 comprising: monitoring, by multiple monitors, physiological states of multiple drivers during multiple learning periods to provide physiological state information regarding the multiple drivers; wherein the physiological state information is indicative of the one or more physiological parameters; receiving or generating indication about dangerous events that occurred during the multiple learning periods; searching for a predicting physiological parameter of the one or more physiological parameters; wherein each predicting physiological parameter is associated with a predicting pattern that was indicative of an occurrence of one of the dangerous events; and when finding the predicting physiological parameter then responding to the finding.

3. The method according to claim 2 wherein the multiple drivers are of a same gender.

4. The method according to claim 1 wherein the predicting physiological parameter is selected from the group consisting of: a yawning rate, a blinking rate, an eyeballs movements rate, a parameter related to head turns, a direction of gaze, and one or more electrocardiogram (ECG) parameters.

5. The method according to claim 1 wherein the responding comprises instructing or requesting at least one monitor of at least one vehicle to monitor at least one driver of the at least one vehicle to search for a future occurrence of the predictive pattern in the predicting physiological parameter.

6. A method for driver-based prediction of dangerous events, the method comprises:

monitoring, by a monitor and during a learning period, a physiological state of a driver to provide physiological state information; wherein the physiological state information represents one or more physiological parameters of the driver;

receiving or generating an indication about a dangerous event that occurred during the learning period;

searching for a predicting physiological parameter of the one or more physiological parameters; wherein the predicting physiological parameter is associated with a predicting pattern that was indicative of an occurrence of the dangerous event; and when finding the predicting physiological parameter then responding to the finding;

wherein the finding of the predictive pattern comprises:

comparing (a) statistics related to values of the predicting physiological parameter during at least a majority of the learning period, and (b) statistics related to values of the predicting physiological parameter at a part of the learning period that preceded the start of the dangerous event.

7. The method according to claim 6 wherein the at least majority comprises the entire learning period.

8. The method according to claim 6 wherein the at least majority excludes a duration of the dangerous event.

9. A method for driver-based prediction of dangerous events, the method comprises:

monitoring, by a monitor and during a learning period, a physiological state of a driver to provide physiological state information; wherein the physiological state information represents one or more physiological parameters of the driver;

receiving or generating an indication about a dangerous event that occurred during the learning period;

searching for a predicting physiological parameter of the one or more physiological parameters; wherein the predicting physiological parameter is associated with a predicting pattern that was indicative of an occurrence of the dangerous event; and when finding the predicting physiological parameter then responding to the finding;

wherein the finding of the predictive pattern comprises:

segmenting a part of the learning period to time segments; wherein the part of the learning period preceded the start of the dangerous event;

calculating statistics related to values of the predicting physiological parameter during each time segment; and comparing (a) statistics related to values of the predicting physiological parameter during at least a majority of the learning period, and (b) the statistics related to values of the predicting physiological parameter during each of the time segments.

10. The method according to claim 9 wherein the time segments are of random length.

11. A non-transitory computer readable medium that stores instructions for:

monitoring, by a monitor and during a learning period, a physiological state of a driver to provide physiological state information; wherein the physiological state information represents one or more physiological parameters of the driver;

receiving or generating an indication about a dangerous event that occurred during the learning period;

searching for a predicting physiological parameter of the one or more physiological parameters; wherein the predicting physiological parameter is associated with a predicting pattern that was indicative of an occurrence of the dangerous event; and when finding the predicting physiological parameter then responding to the finding;

wherein the predictive pattern comprises (a) a change of the predicting physiological parameter within the learning period and at a certain point in time before the occurrence of the dangerous event, and (b) maintaining the predicting physiological parameter, after the certain point in time, changed.

12. The non-transitory computer readable medium according to claim 11 wherein the finding of the predictive pattern comprises:

comparing (a) statistics related to values of the predicting physiological parameter during at least a majority of the learning period, and (b) statistics related to values of the predicting physiological parameter at a part of the learning period that preceded the start of the dangerous event.

13. The non-transitory computer readable medium according to claim 12 wherein the at least majority comprises the entire learning period.

14. The non-transitory computer readable medium according to claim 12 wherein the at least majority excludes a duration of the dangerous event.

15. The non-transitory computer readable medium according to claim 11 wherein the finding of the predictive pattern comprises:

segmenting a part of the learning period to time segments; wherein the part of the learning period preceded the start of the dangerous event;

calculating statistics related to values of the predicting physiological parameter during each time segment; and comparing (a) statistics related to values of the predicting physiological parameter during at least a majority of the learning period, and (b) the statistics related to values of the predicting physiological parameter during each of the time segments.

16. The non-transitory computer readable medium according to claim 15 wherein the time segments are of random length.

17. The non-transitory computer readable medium according to claim 11 that stores instructions for: monitoring, by multiple monitors, physiological states multiple drivers during multiple learning periods to provide physiological state information regarding the multiple drivers; wherein the physiological state information is indicative of the one or more physiological parameters; receiving or generating indication about dangerous events that occurred during the multiple learning periods; searching for a predicting physiological parameter of the one or more physiological parameters; wherein each predicting physiological parameter is associated with a predicting pattern that was indicative of an occurrence of one of the dangerous events; and when finding the predicting physiological parameter then instructing or requesting at least one monitor to monitor at least one driver of at least one vehicle to search for the predicting pattern.

18. The non-transitory computer readable medium according to claim 17 wherein the multiple drivers are of a same gender.

19. The non-transitory computer readable medium according to claim 11 wherein the predicting physiological parameter is selected from the group consisting of: a yawning rate, a blinking rate, an eyeballs movements rate, a parameter related to head turns, a direction of gaze, and one or more electrocardiogram (ECG) parameters.

* * * * *